(12) United States Patent
Frevert et al.

(10) Patent No.: US 10,603,353 B2
(45) Date of Patent: Mar. 31, 2020

(54) RECOMBINANT CLOSTRIDIAL NEUROTOXINS WITH INCREASED DURATION OF EFFECT

(71) Applicant: Merz Pharma GmbH & Co. KGAA, Frankfurt am Main (DE)

(72) Inventors: Jürgen Frevert, Berlin (DE); Fred Hofmann, Schwielowsee (DE); Michael Schmidt, Potsdam (DE); Manuela López De La Paz, Liederbach im Taunus (DE); Daniel Scheps, Potsdam (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 12 days.

(21) Appl. No.: 15/735,417

(22) PCT Filed: Jun. 10, 2016

(86) PCT No.: PCT/EP2016/000962
§ 371 (c)(1),
(2) Date: Dec. 11, 2017

(87) PCT Pub. No.: WO2016/198163
PCT Pub. Date: Dec. 15, 2016

(65) Prior Publication Data
US 2018/0169182 A1 Jun. 21, 2018

(30) Foreign Application Priority Data
Jun. 11, 2015 (EP) ..................... 15001733

(51) Int. Cl.
*A61K 38/16* (2006.01)
*C07K 14/33* (2006.01)
*C12N 15/52* (2006.01)
*A61K 38/00* (2006.01)
*C12N 15/70* (2006.01)

(52) U.S. Cl.
CPC ............ *A61K 38/164* (2013.01); *C07K 14/33* (2013.01); *C12N 15/52* (2013.01); *C12N 15/70* (2013.01); *C12Y 304/24069* (2013.01); *A61K 38/00* (2013.01); *C12Y 304/24068* (2013.01); *Y02A 50/469* (2018.01)

(58) Field of Classification Search
None
See application file for complete search history.

(56) References Cited

U.S. PATENT DOCUMENTS

| | | | |
|---|---|---|---|
| 6,903,187 B1 | 6/2005 | Steward et al. | |
| 8,444,991 B2* | 5/2013 | Randolph | A61K 39/08 424/184.1 |
| 8,563,521 B2* | 10/2013 | Skerra | C07K 14/47 435/320.1 |
| 8,748,151 B2* | 6/2014 | Frevert | C07K 14/33 424/94.1 |
| 8,808,710 B2* | 8/2014 | Randolph | A61K 39/08 424/234.1 |
| 9,260,494 B2* | 2/2016 | Skerra | C07K 14/47 |
| 9,388,394 B2* | 7/2016 | Heinrichs | C07K 14/33 |
| 9,758,573 B2* | 9/2017 | Vartanian | A61K 35/741 |
| 9,827,298 B2* | 11/2017 | Hofmann | C07K 14/33 |
| 9,975,929 B2* | 5/2018 | Frevert | C07K 14/33 |
| 10,022,424 B2* | 7/2018 | Stossel | A61K 38/1709 |
| 2002/0127247 A1 | 9/2002 | Steward et al. | |
| 2015/0044250 A1* | 2/2015 | Heinrichs | C07K 14/33 424/190.1 |
| 2015/0322118 A1* | 11/2015 | Groer | C07K 14/33 514/17.7 |
| 2017/0058006 A1* | 3/2017 | Frevert | C07K 14/33 |
| 2018/0141982 A1* | 5/2018 | Anderson | A61K 8/64 |

(Continued)

FOREIGN PATENT DOCUMENTS

EP 2 369 005 A1 9/2011
WO 95/32738 A1 12/1995

(Continued)

OTHER PUBLICATIONS

PCT International Search Report for PCT/EP2016/000962, dated Sep. 26, 2016.
Schlapschy, et al., "PASylation: a biological alternative to PEGylation for extending the plasma half-life of pharmaceutically active proteins," Protein Engineering, Design and Selection, (2013), vol. 26, No. 8: 489-501.
Weber, "Inhibierung von Stat5 in Tumoren durch RNA-Interferenz und spezifische Interaktion eines Peptidaptamer-Konstruktes mit der DNA-Bindedomäne," PhD thesis, Johann-Wolfgang-Goethe Universität, Frankfurt am Main (Germany) 2013.

(Continued)

*Primary Examiner* — Nita M. Minnifield
(74) *Attorney, Agent, or Firm* — McBee Moore & Vanik IP, LLC

(57) ABSTRACT

This invention relates to novel recombinant clostridial neurotoxins exhibiting increased duration of effect and to methods for the manufacture of such recombinant clostridial neurotoxins. These novel recombinant clostridial neurotoxins comprise a random coil domain, and the methods comprise the steps of inserting a nucleic acid sequence coding for a random coil domain into a nucleic acid sequence coding for a parental clostridial neurotoxin and expression of the recombinant nucleic acid sequence comprising the random coil domain-coding sequence in a host cell. The invention further relates to novel recombinant single-chain precursor clostridial neurotoxins used in such methods, nucleic acid sequences encoding such recombinant single-chain precursor clostridial neurotoxins, and pharmaceutical compositions comprising the recombinant clostridial neurotoxin with increased duration of effect.

27 Claims, 5 Drawing Sheets
(3 of 5 Drawing Sheet(s) Filed in Color)
Specification includes a Sequence Listing.

(56) References Cited

U.S. PATENT DOCUMENTS

| | | | |
|---|---|---|---|
| 2018/0169182 A1* | 6/2018 | Frevert | C07K 14/33 |
| 2018/0327730 A1* | 11/2018 | Hofmann | C07K 14/33 |
| 2019/0256834 A1* | 8/2019 | Dong | C07K 14/33 |
| 2019/0300869 A1* | 10/2019 | Dong | A61K 38/4893 |

FOREIGN PATENT DOCUMENTS

| | | | | |
|---|---|---|---|---|
| WO | 96/39166 A1 | 12/1996 | | |
| WO | 00/12728 A1 | 3/2000 | | |
| WO | 01/14570 A1 | 3/2001 | | |
| WO | 02/08268 A2 | 1/2002 | | |
| WO | 2006/017749 A2 | 2/2006 | | |
| WO | 2006/076902 A2 | 7/2006 | | |
| WO | WO-2008155134 A1 * | 12/2008 | | C07K 14/47 |
| WO | 2011/144756 A1 | 11/2011 | | |
| WO | 2013082116 A1 | 6/2013 | | |
| WO | WO-2013082116 A1 * | 6/2013 | | A61K 38/28 |
| WO | WO-2013112867 A1 * | 8/2013 | | C07K 14/33 |
| WO | 2014086494 A1 | 6/2014 | | |
| WO | WO-2014086494 A1 * | 6/2014 | | C07K 14/33 |
| WO | WO-2015132004 A1 * | 9/2015 | | C07K 14/33 |
| WO | WO-2015183044 A1 * | 12/2015 | | A61K 39/08 |
| WO | WO-2016073562 A1 * | 5/2016 | | C07K 16/1282 |
| WO | WO-2016110662 A1 * | 7/2016 | | A61K 8/64 |
| WO | WO-2016198163 A1 * | 12/2016 | | C07K 14/33 |
| WO | WO-2017125487 A1 * | 7/2017 | | C07K 14/33 |

OTHER PUBLICATIONS

Fernandez-Salas, et al., "Plasma membrane localization signals in the light chain of botulinum neurotoxin," Proc. Natl. Acad. Sci. U.S.A., (2004), vol. 101, No. 9: 3208-3213.

Wang, et al., "A Dileucine in the Protease of Botulinum Toxin a Underlies Its Long-lived Neuroparalysis," J. Biol. Chem., (2011), vol. 286, No. 8: 6375-6385.

Aoki, K.R., "A comparison of the safety margins of botulinum neurotoxin serotypes A, B, and F in mice," Toxicon, (2001), vol. 39: 1815-1820.

* cited by examiner

SEQUENCE LISTING

<160> NUMBER OF SEQ ID NOS: 15

<210> SEQ ID NO 1
<211> LENGTH: 20
<212> TYPE: PRT
<213> ORGANISM: Artificial Sequence
<220> FEATURE:
<223> OTHER INFORMATION: PAS20 sequence_I

<400> SEQUENCE: 1

Ala Ser Pro Ala Ala Pro Ala Pro Ala Ser Pro Ala Ala Pro Ala Pro
1               5                   10                  15

Ser Ala Pro Ala
            20

<210> SEQ ID NO 2
<211> LENGTH: 20
<212> TYPE: PRT
<213> ORGANISM: Artificial Sequence
<220> FEATURE:
<223> OTHER INFORMATION: PAS20 sequence_II

<400> SEQUENCE: 2

Ala Ala Pro Ala Ser Pro Ala Pro Ala Ala Pro Ser Ala Pro Ala Pro
1               5                   10                  15

Ala Ala Pro Ser
            20

<210> SEQ ID NO 3
<211> LENGTH: 20
<212> TYPE: PRT
<213> ORGANISM: Artificial Sequence
<220> FEATURE:
<223> OTHER INFORMATION: PAS20 sequence_III

<400> SEQUENCE: 3

Ala Pro Ser Ser Pro Ser Pro Ser Ala Pro Ser Ser Pro Ser Pro Ala
1               5                   10                  15

Ser Pro Ser Ser
            20

<210> SEQ ID NO 4
<211> LENGTH: 20
<212> TYPE: PRT
<213> ORGANISM: Artificial Sequence

```
<220> FEATURE:
<223> OTHER INFORMATION: PAS20 sequence_IV

<400> SEQUENCE: 4

Ser Ala Pro Ser Ser Pro Ser Pro Ser Ala Pro Ser Ser Pro Ser Pro
1               5                   10                  15

Ala Ser Pro Ser
            20

<210> SEQ ID NO 5
<211> LENGTH: 20
<212> TYPE: PRT
<213> ORGANISM: Artificial Sequence
<220> FEATURE:
<223> OTHER INFORMATION: PAS20 sequence_V

<400> SEQUENCE: 5

Ser Ser Pro Ser Ala Pro Ser Pro Ser Ser Pro Ala Ser Pro Ser Pro
1               5                   10                  15

Ser Ser Pro Ala
            20

<210> SEQ ID NO 6
<211> LENGTH: 24
<212> TYPE: PRT
<213> ORGANISM: Artificial Sequence
<220> FEATURE:
<223> OTHER INFORMATION: PAS24 sequence_I

<400> SEQUENCE: 6

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 7
<211> LENGTH: 20
<212> TYPE: PRT
<213> ORGANISM: Artificial Sequence
<220> FEATURE:
<223> OTHER INFORMATION: PAS20 sequence_VI

<400> SEQUENCE: 7

Ala Ser Ala Ala Ala Pro Ala Ala Ala Ser Ala Ala Ala Ser Ala Pro
1               5                   10                  15

Ser Ala Ala Ala
            20

<210> SEQ ID NO 8
<211> LENGTH: 1546
<212> TYPE: PRT
<213> ORGANISM: Artificial Sequence
<220> FEATURE:
<223> OTHER INFORMATION: PAS200 rBoNT/A: protein sequence

<400> SEQUENCE: 8

Met Gly Ser Ser His His His His His His Gly Ser Leu Val Pro Arg
1               5                   10                  15

Ser Ser Ser Ala Ser Pro Ala Ala Pro Ala Pro Ala Ser Pro Ala Ala
                20                  25                  30

Pro Ala Pro Ser Ala Pro Ala Ala Ser Pro Ala Ala Pro Ala Pro Ala
            35                  40                  45

Ser Pro Ala Ala Pro Ala Pro Ser Ala Pro Ala Ala Ser Pro Ala Ala
```

```
             50                  55                  60
Pro Ala Pro Ala Ser Pro Ala Pro Ala Pro Ser Ala Pro Ala Ala
 65                  70                  75                  80

Ser Pro Ala Ala Pro Ala Pro Ala Ser Pro Ala Ala Pro Ala Pro Ser
                 85                  90                  95

Ala Pro Ala Ala Ser Pro Ala Ala Pro Ala Pro Ala Ser Pro Ala Ala
                100                 105                 110

Pro Ala Pro Ser Ala Pro Ala Ala Ser Pro Ala Ala Pro Ala Pro Ala
                115                 120                 125

Ser Pro Ala Ala Pro Ala Pro Ser Ala Pro Ala Ala Ser Pro Ala Ala
                130                 135                 140

Pro Ala Pro Ala Ser Pro Ala Ala Pro Ala Pro Ser Ala Pro Ala Ala
145                 150                 155                 160

Ser Pro Ala Ala Pro Ala Pro Ala Ser Pro Ala Ala Pro Ala Pro Ser
                165                 170                 175

Ala Pro Ala Ala Ser Pro Ala Ala Pro Ala Pro Ala Ser Pro Ala Ala
                180                 185                 190

Pro Ala Pro Ser Ala Pro Ala Ala Ser Pro Ala Ala Pro Ala Pro Ala
                195                 200                 205

Ser Pro Ala Ala Pro Ala Pro Ser Ala Pro Ala Ala Pro Phe Val Asn
                210                 215                 220

Lys Gln Phe Asn Tyr Lys Asp Pro Val Asn Gly Val Asp Ile Ala Tyr
225                 230                 235                 240

Ile Lys Ile Pro Asn Ala Gly Gln Met Gln Pro Val Lys Ala Phe Lys
                245                 250                 255

Ile His Asn Lys Ile Trp Val Ile Pro Glu Arg Asp Thr Phe Thr Asn
                260                 265                 270

Pro Glu Glu Gly Asp Leu Asn Pro Pro Glu Ala Lys Gln Val Pro
                275                 280                 285

Val Ser Tyr Tyr Asp Ser Thr Tyr Leu Ser Thr Asp Asn Glu Lys Asp
                290                 295                 300

Asn Tyr Leu Lys Gly Val Thr Lys Leu Phe Glu Arg Ile Tyr Ser Thr
305                 310                 315                 320

Asp Leu Gly Arg Met Leu Leu Thr Ser Ile Val Arg Gly Ile Pro Phe
                325                 330                 335

Trp Gly Gly Ser Thr Ile Asp Thr Glu Leu Lys Val Ile Asp Thr Asn
                340                 345                 350

Cys Ile Asn Val Ile Gln Pro Asp Gly Ser Tyr Arg Ser Glu Glu Leu
                355                 360                 365

Asn Leu Val Ile Ile Gly Pro Ser Ala Asp Ile Ile Gln Phe Glu Cys
                370                 375                 380

Lys Ser Phe Gly His Glu Val Leu Asn Leu Thr Arg Asn Gly Tyr Gly
385                 390                 395                 400

Ser Thr Gln Tyr Ile Arg Phe Ser Pro Asp Phe Thr Phe Gly Phe Glu
                405                 410                 415

Glu Ser Leu Glu Val Asp Thr Asn Pro Leu Leu Gly Ala Gly Lys Phe
                420                 425                 430

Ala Thr Asp Pro Ala Val Thr Leu Ala His Glu Leu Ile His Ala Gly
                435                 440                 445

His Arg Leu Tyr Gly Ile Ala Ile Asn Pro Asn Arg Val Phe Lys Val
                450                 455                 460

Asn Thr Asn Ala Tyr Tyr Glu Met Ser Gly Leu Glu Val Ser Phe Glu
465                 470                 475                 480
```

```
Glu Leu Arg Thr Phe Gly Gly His Asp Ala Lys Phe Ile Asp Ser Leu
            485                 490                 495

Gln Glu Asn Glu Phe Arg Leu Tyr Tyr Tyr Asn Lys Phe Lys Asp Ile
            500                 505                 510

Ala Ser Thr Leu Asn Lys Ala Lys Ser Ile Val Gly Thr Thr Ala Ser
            515                 520                 525

Leu Gln Tyr Met Lys Asn Val Phe Lys Glu Lys Tyr Leu Leu Ser Glu
            530                 535                 540

Asp Thr Ser Gly Lys Phe Ser Val Asp Lys Leu Lys Phe Asp Lys Leu
545                 550                 555                 560

Tyr Lys Met Leu Thr Glu Ile Tyr Thr Glu Asp Asn Phe Val Lys Phe
                565                 570                 575

Phe Lys Val Leu Asn Arg Lys Thr Tyr Leu Asn Phe Asp Lys Ala Val
                580                 585                 590

Phe Lys Ile Asn Ile Val Pro Lys Val Asn Tyr Thr Ile Tyr Asp Gly
                595                 600                 605

Phe Asn Leu Arg Asn Thr Asn Leu Ala Ala Asn Phe Asn Gly Gln Asn
                610                 615                 620

Thr Glu Ile Asn Asn Met Asn Phe Thr Lys Leu Lys Asn Phe Thr Gly
625                 630                 635                 640

Leu Phe Glu Phe Tyr Lys Leu Leu Cys Val Arg Gly Ile Ile Thr Ser
                645                 650                 655

Lys Ala Gly Ala Gly Lys Ser Leu Val Pro Arg Gly Ser Ala Gly Ala
                660                 665                 670

Gly Ala Leu Asn Asp Leu Cys Ile Lys Val Asn Asn Trp Asp Leu Phe
                675                 680                 685

Phe Ser Pro Ser Glu Asp Asn Phe Thr Asn Asp Leu Asn Lys Gly Glu
            690                 695                 700

Glu Ile Thr Ser Asp Thr Asn Ile Glu Ala Ala Glu Asn Ile Ser
705                 710                 715                 720

Leu Asp Leu Ile Gln Gln Tyr Tyr Leu Thr Phe Asn Phe Asp Asn Glu
                725                 730                 735

Pro Glu Asn Ile Ser Ile Glu Asn Leu Ser Ser Asp Ile Ile Gly Gln
                740                 745                 750

Leu Glu Leu Met Pro Asn Ile Glu Arg Phe Pro Asn Gly Lys Lys Tyr
                755                 760                 765

Glu Leu Asp Lys Tyr Thr Met Phe His Tyr Leu Arg Ala Gln Glu Phe
            770                 775                 780

Glu His Gly Lys Ser Arg Ile Ala Leu Thr Asn Ser Val Asn Glu Ala
785                 790                 795                 800

Leu Leu Asn Pro Ser Arg Val Tyr Thr Phe Phe Ser Ser Asp Tyr Val
                805                 810                 815

Lys Lys Val Asn Lys Ala Thr Glu Ala Ala Met Phe Leu Gly Trp Val
                820                 825                 830

Glu Gln Leu Val Tyr Asp Phe Thr Asp Glu Thr Ser Glu Val Ser Thr
                835                 840                 845

Thr Asp Lys Ile Ala Asp Ile Thr Ile Ile Pro Tyr Ile Gly Pro
850                 855                 860

Ala Leu Asn Ile Gly Asn Met Leu Tyr Lys Asp Asp Phe Val Gly Ala
865                 870                 875                 880

Leu Ile Phe Ser Gly Ala Val Ile Leu Leu Glu Phe Ile Pro Glu Ile
                885                 890                 895
```

-continued

```
Ala Ile Pro Val Leu Gly Thr Phe Ala Leu Val Ser Tyr Ile Ala Asn
            900                 905                 910

Lys Val Leu Thr Val Gln Thr Ile Asp Asn Ala Leu Ser Lys Arg Asn
        915                 920                 925

Glu Lys Trp Asp Glu Val Tyr Lys Tyr Ile Val Thr Asn Trp Leu Ala
    930                 935                 940

Lys Val Asn Thr Gln Ile Asp Leu Ile Arg Lys Lys Met Lys Glu Ala
945                 950                 955                 960

Leu Glu Asn Gln Ala Glu Ala Thr Lys Ala Ile Ile Asn Tyr Gln Tyr
                965                 970                 975

Asn Gln Tyr Thr Glu Glu Lys Asn Asn Ile Asn Phe Asn Ile Asp
            980                 985                 990

Asp Leu Ser Ser Lys Leu Asn Glu Ser Ile Asn Lys Ala Met Ile Asn
            995                 1000                1005

Ile Asn Lys Phe Leu Asn Gln Cys Ser Val Ser Tyr Leu Met Asn
    1010                1015                1020

Ser Met Ile Pro Tyr Gly Val Lys Arg Leu Glu Asp Phe Asp Ala
    1025                1030                1035

Ser Leu Lys Asp Ala Leu Leu Lys Tyr Ile Tyr Asp Asn Arg Gly
    1040                1045                1050

Thr Leu Ile Gly Gln Val Asp Arg Leu Lys Asp Lys Val Asn Asn
    1055                1060                1065

Thr Leu Ser Thr Asp Ile Pro Phe Gln Leu Ser Lys Tyr Val Asp
    1070                1075                1080

Asn Gln Arg Leu Leu Ser Thr Phe Thr Glu Tyr Ile Lys Asn Ile
    1085                1090                1095

Ile Asn Thr Ser Ile Leu Asn Leu Arg Tyr Glu Ser Asn His Leu
    1100                1105                1110

Ile Asp Leu Ser Arg Tyr Ala Ser Lys Ile Asn Ile Gly Ser Lys
    1115                1120                1125

Val Asn Phe Asp Pro Ile Asp Lys Asn Gln Ile Gln Leu Phe Asn
    1130                1135                1140

Leu Glu Ser Ser Lys Ile Glu Val Ile Leu Lys Asn Ala Ile Val
    1145                1150                1155

Tyr Asn Ser Met Tyr Glu Asn Phe Ser Thr Ser Phe Trp Ile Arg
    1160                1165                1170

Ile Pro Lys Tyr Phe Asn Ser Ile Ser Leu Asn Asn Glu Tyr Thr
    1175                1180                1185

Ile Ile Asn Cys Met Glu Asn Asn Ser Gly Trp Lys Val Ser Leu
    1190                1195                1200

Asn Tyr Gly Glu Ile Ile Trp Thr Leu Gln Asp Thr Gln Glu Ile
    1205                1210                1215

Lys Gln Arg Val Val Phe Lys Tyr Ser Gln Met Ile Asn Ile Ser
    1220                1225                1230

Asp Tyr Ile Asn Arg Trp Ile Phe Val Thr Ile Thr Asn Asn Arg
    1235                1240                1245

Leu Asn Asn Ser Lys Ile Tyr Ile Asn Gly Arg Leu Ile Asp Gln
    1250                1255                1260

Lys Pro Ile Ser Asn Leu Gly Asn Ile His Ala Ser Asn Asn Ile
    1265                1270                1275

Met Phe Lys Leu Asp Gly Cys Arg Asp Thr His Arg Tyr Ile Trp
    1280                1285                1290

Ile Lys Tyr Phe Asn Leu Phe Asp Lys Glu Leu Asn Glu Lys Glu
```

```
            1295                1300                1305

Ile Lys Asp Leu Tyr Asp Asn Gln Ser Asn Ser Gly Ile Leu Lys
        1310                1315                1320

Asp Phe Trp Gly Asp Tyr Leu Gln Tyr Asp Lys Pro Tyr Tyr Met
    1325                1330                1335

Leu Asn Leu Tyr Asp Pro Asn Lys Tyr Val Asp Val Asn Asn Val
1340                1345                1350

Gly Ile Arg Gly Tyr Met Tyr Leu Lys Gly Pro Arg Gly Ser Val
        1355                1360                1365

Met Thr Thr Asn Ile Tyr Leu Asn Ser Ser Leu Tyr Arg Gly Thr
    1370                1375                1380

Lys Phe Ile Ile Lys Lys Tyr Ala Ser Gly Asn Lys Asp Asn Ile
1385                1390                1395

Val Arg Asn Asn Asp Arg Val Tyr Ile Asn Val Val Lys Asn
        1400                1405                1410

Lys Glu Tyr Arg Leu Ala Thr Asn Ala Ser Gln Ala Gly Val Glu
    1415                1420                1425

Lys Ile Leu Ser Ala Leu Glu Ile Pro Asp Val Gly Asn Leu Ser
1430                1435                1440

Gln Val Val Met Lys Ser Lys Asn Asp Gln Gly Ile Thr Asn
        1445                1450                1455

Lys Cys Lys Met Asn Leu Gln Asp Asn Asn Gly Asn Asp Ile Gly
    1460                1465                1470

Phe Ile Gly Phe His Gln Phe Asn Asn Ile Ala Lys Leu Val Ala
1475                1480                1485

Ser Asn Trp Tyr Asn Arg Gln Ile Glu Arg Ser Ser Arg Thr Leu
        1490                1495                1500

Gly Cys Ser Trp Glu Phe Ile Pro Val Asp Asp Gly Trp Gly Glu
    1505                1510                1515

Arg Pro Leu Gly Asp Leu Val Pro Arg Gly Ser Ala Asn Ser Ser
1520                1525                1530

Ser Val Asp Lys Leu Trp Ser His Pro Gln Phe Glu Lys
        1535                1540                1545

<210> SEQ ID NO 9
<211> LENGTH: 1446
<212> TYPE: PRT
<213> ORGANISM: Artificial Sequence
<220> FEATURE:
<223> OTHER INFORMATION: PAS100 rBoNT/A: protein sequence

<400> SEQUENCE: 9

Met Gly Ser Ser His His His His His His Gly Ser Leu Val Pro Arg
1               5                   10                  15

Ser Ser Ser Ala Ser Pro Ala Ala Pro Ala Pro Ala Ser Pro Ala Ala
            20                  25                  30

Pro Ala Pro Ser Ala Pro Ala Ala Ser Pro Ala Ala Pro Ala Pro Ala
        35                  40                  45

Ser Pro Ala Ala Pro Ala Pro Ser Ala Pro Ala Ala Ser Pro Ala Ala
    50                  55                  60

Pro Ala Pro Ala Ser Pro Ala Ala Pro Ala Pro Ser Ala Pro Ala Ala
65                  70                  75                  80

Ser Pro Ala Ala Pro Ala Pro Ala Ser Pro Ala Ala Pro Ala Pro Ser
                85                  90                  95

Ala Pro Ala Ala Ser Pro Ala Ala Pro Ala Pro Ala Ser Pro Ala Ala
```

-continued

```
                100                 105                 110
Pro Ala Pro Ser Ala Pro Ala Pro Phe Val Asn Lys Gln Phe Asn
            115                 120                 125
Tyr Lys Asp Pro Val Asn Gly Val Asp Ile Ala Tyr Ile Lys Ile Pro
        130                 135                 140
Asn Ala Gly Gln Met Gln Pro Val Lys Ala Phe Lys Ile His Asn Lys
145                 150                 155                 160
Ile Trp Val Ile Pro Glu Arg Asp Thr Phe Thr Asn Pro Glu Glu Gly
                165                 170                 175
Asp Leu Asn Pro Pro Glu Ala Lys Gln Val Pro Val Ser Tyr Tyr
            180                 185                 190
Asp Ser Thr Tyr Leu Ser Thr Asp Asn Glu Lys Asp Asn Tyr Leu Lys
        195                 200                 205
Gly Val Thr Lys Leu Phe Glu Arg Ile Tyr Ser Thr Asp Leu Gly Arg
    210                 215                 220
Met Leu Leu Thr Ser Ile Val Arg Gly Ile Pro Phe Trp Gly Gly Ser
225                 230                 235                 240
Thr Ile Asp Thr Glu Leu Lys Val Ile Asp Thr Asn Cys Ile Asn Val
                245                 250                 255
Ile Gln Pro Asp Gly Ser Tyr Arg Ser Glu Glu Leu Asn Leu Val Ile
            260                 265                 270
Ile Gly Pro Ser Ala Asp Ile Ile Gln Phe Glu Cys Lys Ser Phe Gly
        275                 280                 285
His Glu Val Leu Asn Leu Thr Arg Asn Gly Tyr Gly Ser Thr Gln Tyr
    290                 295                 300
Ile Arg Phe Ser Pro Asp Phe Thr Phe Gly Phe Glu Glu Ser Leu Glu
305                 310                 315                 320
Val Asp Thr Asn Pro Leu Leu Gly Ala Gly Lys Phe Ala Thr Asp Pro
                325                 330                 335
Ala Val Thr Leu Ala His Glu Leu Ile His Ala Gly His Arg Leu Tyr
            340                 345                 350
Gly Ile Ala Ile Asn Pro Asn Arg Val Phe Lys Val Asn Thr Asn Ala
        355                 360                 365
Tyr Tyr Glu Met Ser Gly Leu Glu Val Ser Phe Glu Glu Leu Arg Thr
    370                 375                 380
Phe Gly Gly His Asp Ala Lys Phe Ile Asp Ser Leu Gln Glu Asn Glu
385                 390                 395                 400
Phe Arg Leu Tyr Tyr Tyr Asn Lys Phe Lys Asp Ile Ala Ser Thr Leu
                405                 410                 415
Asn Lys Ala Lys Ser Ile Val Gly Thr Thr Ala Ser Leu Gln Tyr Met
            420                 425                 430
Lys Asn Val Phe Lys Glu Lys Tyr Leu Leu Ser Glu Asp Thr Ser Gly
        435                 440                 445
Lys Phe Ser Val Asp Lys Leu Lys Phe Asp Lys Leu Tyr Lys Met Leu
    450                 455                 460
Thr Glu Ile Tyr Thr Glu Asp Asn Phe Val Lys Phe Phe Lys Val Leu
465                 470                 475                 480
Asn Arg Lys Thr Tyr Leu Asn Phe Asp Lys Ala Val Phe Lys Ile Asn
                485                 490                 495
Ile Val Pro Lys Val Asn Tyr Thr Ile Tyr Asp Gly Phe Asn Leu Arg
            500                 505                 510
Asn Thr Asn Leu Ala Ala Asn Phe Asn Gly Gln Asn Thr Glu Ile Asn
        515                 520                 525
```

-continued

```
Asn Met Asn Phe Thr Lys Leu Lys Asn Phe Thr Gly Leu Phe Glu Phe
    530                 535                 540

Tyr Lys Leu Leu Cys Val Arg Gly Ile Ile Thr Ser Lys Ala Gly Ala
545                 550                 555                 560

Gly Lys Ser Leu Val Pro Arg Gly Ser Ala Gly Ala Gly Ala Leu Asn
                565                 570                 575

Asp Leu Cys Ile Lys Val Asn Asn Trp Asp Leu Phe Phe Ser Pro Ser
            580                 585                 590

Glu Asp Asn Phe Thr Asn Asp Leu Asn Lys Gly Glu Glu Ile Thr Ser
                595                 600                 605

Asp Thr Asn Ile Glu Ala Ala Glu Glu Asn Ile Ser Leu Asp Leu Ile
    610                 615                 620

Gln Gln Tyr Tyr Leu Thr Phe Asn Phe Asp Asn Glu Pro Glu Asn Ile
625                 630                 635                 640

Ser Ile Glu Asn Leu Ser Ser Asp Ile Ile Gly Gln Leu Glu Leu Met
                645                 650                 655

Pro Asn Ile Glu Arg Phe Pro Asn Gly Lys Lys Tyr Glu Leu Asp Lys
                660                 665                 670

Tyr Thr Met Phe His Tyr Leu Arg Ala Gln Glu Phe Glu His Gly Lys
            675                 680                 685

Ser Arg Ile Ala Leu Thr Asn Ser Val Asn Glu Ala Leu Leu Asn Pro
    690                 695                 700

Ser Arg Val Tyr Thr Phe Phe Ser Ser Asp Tyr Val Lys Lys Val Asn
705                 710                 715                 720

Lys Ala Thr Glu Ala Ala Met Phe Leu Gly Trp Val Glu Gln Leu Val
                725                 730                 735

Tyr Asp Phe Thr Asp Glu Thr Ser Glu Val Ser Thr Thr Asp Lys Ile
            740                 745                 750

Ala Asp Ile Thr Ile Ile Ile Pro Tyr Ile Gly Pro Ala Leu Asn Ile
    755                 760                 765

Gly Asn Met Leu Tyr Lys Asp Asp Phe Val Gly Ala Leu Ile Phe Ser
770                 775                 780

Gly Ala Val Ile Leu Leu Glu Phe Ile Pro Glu Ile Ala Ile Pro Val
785                 790                 795                 800

Leu Gly Thr Phe Ala Leu Val Ser Tyr Ile Ala Asn Lys Val Leu Thr
                805                 810                 815

Val Gln Thr Ile Asp Asn Ala Leu Ser Lys Arg Asn Glu Lys Trp Asp
            820                 825                 830

Glu Val Tyr Lys Tyr Ile Val Thr Asn Trp Leu Ala Lys Val Asn Thr
                835                 840                 845

Gln Ile Asp Leu Ile Arg Lys Lys Met Lys Glu Ala Leu Glu Asn Gln
    850                 855                 860

Ala Glu Ala Thr Lys Ala Ile Ile Asn Tyr Gln Tyr Asn Gln Tyr Thr
865                 870                 875                 880

Glu Glu Glu Lys Asn Asn Ile Asn Phe Asn Ile Asp Asp Leu Ser Ser
                885                 890                 895

Lys Leu Asn Glu Ser Ile Asn Lys Ala Met Ile Asn Ile Asn Lys Phe
                900                 905                 910

Leu Asn Gln Cys Ser Val Ser Tyr Leu Met Asn Ser Met Ile Pro Tyr
            915                 920                 925

Gly Val Lys Arg Leu Glu Asp Phe Asp Ala Ser Leu Lys Asp Ala Leu
    930                 935                 940
```

```
Leu Lys Tyr Ile Tyr Asp Asn Arg Gly Thr Leu Ile Gly Gln Val Asp
945                 950                 955                 960

Arg Leu Lys Asp Lys Val Asn Asn Thr Leu Ser Thr Asp Ile Pro Phe
            965                 970                 975

Gln Leu Ser Lys Tyr Val Asp Asn Gln Arg Leu Leu Ser Thr Phe Thr
                980                 985                 990

Glu Tyr Ile Lys Asn Ile Ile Asn Thr Ser Ile Leu Asn Leu Arg Tyr
        995                 1000                1005

Glu Ser Asn His Leu Ile Asp Leu Ser Arg Tyr Ala Ser Lys Ile
    1010                1015                1020

Asn Ile Gly Ser Lys Val Asn Phe Asp Pro Ile Asp Lys Asn Gln
    1025                1030                1035

Ile Gln Leu Phe Asn Leu Glu Ser Ser Lys Ile Glu Val Ile Leu
    1040                1045                1050

Lys Asn Ala Ile Val Tyr Asn Ser Met Tyr Glu Asn Phe Ser Thr
    1055                1060                1065

Ser Phe Trp Ile Arg Ile Pro Lys Tyr Phe Asn Ser Ile Ser Leu
    1070                1075                1080

Asn Asn Glu Tyr Thr Ile Ile Asn Cys Met Glu Asn Asn Ser Gly
    1085                1090                1095

Trp Lys Val Ser Leu Asn Tyr Gly Glu Ile Ile Trp Thr Leu Gln
    1100                1105                1110

Asp Thr Gln Glu Ile Lys Gln Arg Val Val Phe Lys Tyr Ser Gln
    1115                1120                1125

Met Ile Asn Ile Ser Asp Tyr Ile Asn Arg Trp Ile Phe Val Thr
    1130                1135                1140

Ile Thr Asn Asn Arg Leu Asn Asn Ser Lys Ile Tyr Ile Asn Gly
    1145                1150                1155

Arg Leu Ile Asp Gln Lys Pro Ile Ser Asn Leu Gly Asn Ile His
    1160                1165                1170

Ala Ser Asn Asn Ile Met Phe Lys Leu Asp Gly Cys Arg Asp Thr
    1175                1180                1185

His Arg Tyr Ile Trp Ile Lys Tyr Phe Asn Leu Phe Asp Lys Glu
    1190                1195                1200

Leu Asn Glu Lys Glu Ile Lys Asp Leu Tyr Asp Asn Gln Ser Asn
    1205                1210                1215

Ser Gly Ile Leu Lys Asp Phe Trp Gly Asp Tyr Leu Gln Tyr Asp
    1220                1225                1230

Lys Pro Tyr Tyr Met Leu Asn Leu Tyr Asp Pro Asn Lys Tyr Val
    1235                1240                1245

Asp Val Asn Asn Val Gly Ile Arg Gly Tyr Met Tyr Leu Lys Gly
    1250                1255                1260

Pro Arg Gly Ser Val Met Thr Thr Asn Ile Tyr Leu Asn Ser Ser
    1265                1270                1275

Leu Tyr Arg Gly Thr Lys Phe Ile Ile Lys Lys Tyr Ala Ser Gly
    1280                1285                1290

Asn Lys Asp Asn Ile Val Arg Asn Asn Asp Arg Val Tyr Ile Asn
    1295                1300                1305

Val Val Val Lys Asn Lys Glu Tyr Arg Leu Ala Thr Asn Ala Ser
    1310                1315                1320

Gln Ala Gly Val Glu Lys Ile Leu Ser Ala Leu Glu Ile Pro Asp
    1325                1330                1335

Val Gly Asn Leu Ser Gln Val Val Val Met Lys Ser Lys Asn Asp
```

```
            1340                1345                1350
Gln Gly Ile Thr Asn Lys Cys Lys Met Asn Leu Gln Asp Asn Asn
    1355                1360                1365

Gly Asn Asp Ile Gly Phe Ile Gly Phe His Gln Phe Asn Asn Ile
    1370                1375                1380

Ala Lys Leu Val Ala Ser Asn Trp Tyr Asn Arg Gln Ile Glu Arg
    1385                1390                1395

Ser Ser Arg Thr Leu Gly Cys Ser Trp Glu Phe Ile Pro Val Asp
    1400                1405                1410

Asp Gly Trp Gly Glu Arg Pro Leu Gly Asp Leu Val Pro Arg Gly
    1415                1420                1425

Ser Ala Asn Ser Ser Ser Val Asp Lys Leu Trp Ser His Pro Gln
    1430                1435                1440

Phe Glu Lys
    1445

<210> SEQ ID NO 10
<211> LENGTH: 4641
<212> TYPE: DNA
<213> ORGANISM: Artificial Sequence
<220> FEATURE:
<223> OTHER INFORMATION: PAS200 rBoNT/A: DNA sequence

<400> SEQUENCE: 10
atgggcagca gccatcatca tcaccatcat ggtagcctgg ttccgcgtag ctcttctgca      60
agtccggcag caccggcacc ggcttcacca gctgcaccag cacctagcgc accggcagca     120
tctccagcag cccctgcacc ggcaagccct gcagctccag caccgtcagc accagcagca     180 agccagctg ctcctgctcc agcgagccca gcagcgccag ctcctagtgc ccctgctgcc     240
tctcctgctg ctccggcacc agcaagtcct gctgcgcctg caccgagtgc tccggctgct     300
agtcctgccg caccagctcc ggctagtcca gctgctccag cccctcagc tccggcagct     360 tccctgcag cgcctgcccc tgccagtcca gcggctcctg cacctagtgc gcctgcagct     420
tcaccggctg cccctgcgcc agcttctcct gcggctccag ctccatctgc ccagccgca     480 tccccagcgg caccagctcc agcttctccg gcagcgccag caccttctgc gctgccgca     540 tctcctgcag caccagcgcc tgcgagtcct gcagctcctg ctccttcagc ccctgcggca     600
agtccagcag caccagcccc agcaagccca gccgcaccag caccatctgc ccctgcagca     660
ccatttgtga acaagcagtt taactataag gacccggtga acgtgtggaa tatcgcgtat     720
atcaaaatcc gaatgcgggg ccagatgcaa ccagtcaagg cgttcaagat tcataacaag     780
atttgggtta ttccggaacg tgatacctt caccatccgg aagaaggcga cttaaacccg     840
ccgccagaag ccaaacaagt gccggtgagc tactatgata gcacgtatct tagcaccgat     900
aatgaaaaag acaattacct gaagggcgtg accaagttgt cgagcgcat ctacagtacc     960 gacttaggcc gcatgttgtt gacgagcatc gttcgcggta tcccgttctg ggcggctcg     1020 accattgata ccgagttgaa agtcattgac acgaactgta tcaatgttat ccaaccggac     1080
ggcagttatc gcagcgagga gttaaatttg gtcatcatcg gtccaagcgc agatattatt     1140
cagttcgaat gcaagagctt cggccatgag gtcttgaatt tgacgcgcaa cggttacggc     1200
agcacccaat acatccgctt tagcccggat ttcaccttg gcttcgagga gagcttggag     1260
gtggacacca acccgctgtt aggtgccgga aaattcgcaa cgaccccggc agtgacgttg     1320
gcgcacgaat tgattcatgc gggtcaccgc ttatacggta tcgcgatcaa tccgaatcgc     1380
```

-continued

```
gtctttaaag tcaataccaa cgcgtactac gaaatgagcg gcttagaggt tagctttgaa    1440
gaattacgca ccttcggtgg ccacgacgcc aagttcatcg acagcctgca ggaaaatgag    1500
ttccgcttgt actattacaa taaattcaag gacatcgcga gcaccttaaa taaagcaaag    1560
agcattgtgg gcaccaccgc aagcttgcag tacatgaaga acgtatttaa ggaaaaatat    1620
ttgttgtcgg aggataccag cgggaaattc agcgtcgata agctgaaatt cgacaaattg    1680
tataaaatgc tgaccgagat ttacaccgag gataacttcg tcaagttttt taaggtgtta    1740
aatcgtaaga cctattttaaa ctttgataaa gcggtgttta aaattaatat cgtgccgaag    1800
gtgaattaca ccatctacga tggtttcaat ttacgcaaca cgaatctggc ggcgaatttt    1860
aatggccaaa acaccgaaat taacaacatg aactttacga agttaaagaa tttcacgggc    1920
ttattcgaat tctacaagtt attatgcgtg cgcggcatca ttaccagcaa ggcaggtgcg    1980
ggcaagtcct tggttccgcg tggcagcgcc ggcgccggcg cgctcaatga tctgtgtatt    2040
aaagtcaata actgggacct gttcttcagc ccgagcgagg ataactttac caacgactta    2100
aacaaaggcg aggagatcac gagcgatacg aacatcgagg cggcggagga aaatattagc    2160
ctggacctca ttcagcagta ctatctgacg ttcaattttg acaatgagcc ggagaacatc    2220
agcattgaaa atctcagcag cgacatcatc ggtcagttgg aactgatgcc gaacattgaa    2280
cgctttccga acggcaaaaa atatgaactg acaagtata ccatgttcca ttacttacgc    2340
gcacaggaat tgagcacgg caagagccgc attgcgctga ccaatagcgt taacgaggcc    2400
ttgttaaatc cgagccgtgt ctacacgttc ttcagcagcg attatgtcaa aaaagtgaac    2460
aaggcgaccg aagccgcgat gttttttggc tgggtcgagc aattggttta cgattttacc    2520
gacgaaacca gcgaggtgag cacgaccgac aaaattgcag atatcaccat catcattccg    2580
tacatcggtc cggcgctcaa tatcggcaat atgttataca aggacgactt tgtgggcgcg    2640
ctgatctttta gcggcgcggt tatcttatta gaattcatcc cggagatcgc aatcccggtc    2700
ttgggcacct ttgcgttggt gagctatatc gcgaataaag tgctcacggt ccaaaccatc    2760
gataacgcgc tcagcaagcg taatgagaaa tgggacgagg tttataagta tatcgtgacc    2820
aactggttag caaaagtcaa tacgcagatc gatctcatcc gcaaaaaaat gaagaagcc    2880
ttggaaaatc aagcggaggc aaccaaagcc atcattaatt accagtataa ccaatatacc    2940
gaagaagaaa aaacaatat caacttcaat atcgatgatt tgagcagcaa actgaacgag    3000
agcattaaca aagcgatgat taacatcaac aagttcttga atcaatgcag cgtgagctat    3060
ctcatgaaca gcatgatccc gtatggcgtc aaacgcttgg aagattttga cgccagcctg    3120
aaagatgcgc tcctcaagta tatttatgac aaccgcggca ccctcattgg ccaggtggac    3180
cgcttgaagg ataaagtgaa caatacgctc agcacggata tcccgttcca gctgagcaag    3240
tacgtcgaca ccagcgcttt actgagcacc tttaccgagt atatcaagaa catcattaat    3300
accagcatcc tcaacttgcg ctatgagagc aatcacctga tcgacctcag ccgctacgcc    3360
agcaagatca acatcggcag caaggtcaat ttcgaccccga tcgataagaa tcagatccaa    3420
ttgtttaacc tggaaagcag caagatcgag gttatcttga agaacgcgat tgtgtacaac    3480
agcatgtacg agaactttag cacgagcttc tggattcgta tcccgaagta tttcaatagc    3540
attagcctga ataacgaata taccattatc aactgcatgg aaaataatag cggctggaag    3600
gtgagcttaa attcggcga gatcatttgg accttacagg ataccaaga aatcaaacag    3660
cgcgtcgtct ttaagtatag ccagatgatc aacatcagcg attacatcaa ccgctggatc    3720
ttcgtgacca tcaccaataa tcgcttgaat aatagcaaga tttacatcaa tggtcgcttg    3780
```

```
attgatcaaa aaccgatcag caatctcggt aatatccatg ccagcaataa catcatgttt    3840
aagttagacg gttgccgcga tacccaccgc tatatctgga tcaagtattt taacttattt    3900
gataaggaac tcaacgaaaa ggaaattaaa gacttatatg acaatcagag caatagcggc    3960
atcctgaagg atttctgggg cgactacctg cagtacgata agccgtacta tatgttgaac    4020
ttgtatgacc cgaacaaata tgtcgatgtg aacaatgtgg gtattcgtgg ctatatgtac    4080
ttaaagggcc cgcgtggtag cgtgatgacc acgaatattt acttaaacag cagcttatac    4140
cgcggcacga agtttattat caagaagtat gccagcggca acaaggacaa tatcgtccgc    4200
aacaacgacc gtgtgtatat taacgtggtg gtgaagaata aagagtaccg cttggccacg    4260
aatgcgagcc aggcgggcgt ggaaaaaatc ttgagcgcgt tggagatccc ggacgtcggc    4320
aacctcagcc aggttgtggt gatgaagtct aaaaacgacc agggcatcac gaacaagtgc    4380
aaaatgaatt tgcaagataa caacggcaac gacatcggct ttattggttt tcaccagttc    4440
aataacatcg ccaaactcgt ggccagcaat tggtataacc gccaaattga acgcagcagc    4500
cgcacgctcg gctgtagctg ggagttcatc ccggtggacg atggctgggg cgagcgcccg    4560
ctcggagatc tggtgccacg cggttccgcg aattcgagct ccgtcgacaa gctttggagc    4620
cacccgcagt tcgaaaaata a                                              4641
```

<210> SEQ ID NO 11  
<211> LENGTH: 4341  
<212> TYPE: DNA  
<213> ORGANISM: Artificial Sequence  
<220> FEATURE:  
<223> OTHER INFORMATION: PAS100 rBoNT/A: DNA sequence

<400> SEQUENCE: 11

```
atgggtagca gccatcatca tcaccatcat ggtagcctgg ttccgcgtag ctcttctgca      60
agtccggcag caccggcacc ggcttcacca gctgcaccag cacctagcgc accggcagca     120
tctccagcag cccctgcacc ggcaagccct gcagctccag caccgtcagc accagcagca     180
agcccagctg ctcctgctcc agcgagccca gcagcgccag ctcctagtgc ccctgctgcc     240
tctcctgctg ctccggcacc agcaagtcct gctgcgcctg caccgagtgc tccggctgct     300
agtcctgccg caccagctcc ggctagtcca gctgctccag cccctcagcc cctgcagca     360 ccatttgtga acaagcagtt taactataag gacccggtga acgtgtggga tatcgcgtat     420
atcaaaatcc gaatgcgggg ccagatgcaa ccagtcaagg cgttcaagat tcataacaag     480
atttgggtta ttccggaacg tgatacccttc accaatccgg aagaaggcga tttaaatccg     540
ccgccagaag ccaaacaagt gccggtgagc tactatgata gcacgtatct tagcaccgat     600
aatgaaaaag acaattacct gaagggcgtg accaagttgt cgagcgcat ctacagtacc     660 gacttaggcc gcatgttgtt gacgagcatc gttcgcggta tcccgttctg gggcggctcg     720
accattgata ccgagttgaa agtcattgac acgaactgta tcaatgttat ccaaccggac     780
ggcagttatc gcagcgagga gttaaattcg gtcatcatcg gtccaagcgc agatattatt     840
cagttcgaat gcaagagctt cggccatgag gtcttgaatt tgacgcgcaa cggttacggc     900
agcacccaat acatccgctt tagcccggat ttcaccttg gcttcgagga gagcttggag     960
gtggacacca cccgctgtt aggtgccggc aaattcgcaa ccgacccggc agtgacgttg    1020
gcgcacgaat tgattcatgc gggtcaccgc ttatacggta tcgcgatcaa tccgaatcgc    1080
gtctttaaag tcaataccaa cgcgtactac gaaatgagcg gcttagaggt tagctttgaa    1140
```

-continued

```
gaattacgca ccttcggtgg ccacgacgcc aagttcatcg acagcctgca ggaaaatgag      1200
ttccgcttgt actattacaa taaattcaag gacatcgcga gcaccttaaa taaagcaaag      1260
agcattgtgg gcaccaccgc aagcttgcag tacatgaaga acgtatttaa ggaaaaatat      1320
ttgttgtcgg aggataccag cgggaaattc agcgtcgata agctgaaatt cgacaaattg      1380
tataaaatgc tgaccgagat ttacaccgag gataacttcg tcaagttttt taaggtgtta      1440
aatcgtaaga cctatttaaa ctttgataaa gcggtgttta aaattaatat cgtgccgaag      1500
gtgaattaca ccatctacga tggtttcaat ttacgcaaca cgaatctggc ggcgaatttt      1560
aatggccaaa acaccgaaat taacaacatg aactttacga agttaaagaa tttcacgggc      1620
ttattcgaat tctacaagtt attatgcgtg cgcggcatca ttaccagcaa ggcaggtgcg      1680
ggcaagtcct tggttccgcg tggcagcgcc ggcgccggcg cgctcaatga tctgtgtatt      1740
aaagtcaata actgggacct gttcttcagc ccgagcgagg ataactttac caacgactta      1800
aacaaaggcg aggagatcac gagcgatacg aacatcgagg cggcggagga aaatattagc      1860
ctggacctca ttcagcagta ctatctgacg ttcaattttg acaatgagcc ggagaacatc      1920
agcattgaaa atctcagcag cgacatcatc ggtcagttgg aactgatgcc gaacattgaa      1980
cgctttccga acgcaaaaa atatgaactg gacaagtata ccatgttcca ttacttacgc      2040
gcacaggaat ttgagcacgg caagagccgc attgcgctga ccaatagcgt taacgaggcc      2100
ttgttaaatc cgagccgtgt ctacacgttc ttcagcagcg attatgtcaa aaaagtgaac      2160
aaggcgaccg aagccgcgat gttttttgggc tgggtcgagc aattggttta cgattttacc      2220
gacgaaacca gcgaggtgag cacgaccgac aaaattgcag atatcaccat catcattccg      2280
tacatcggtc cggcgctcaa tatcggcaat atgttataca aggacgactt tgtgggcgcg      2340
ctgatcttta gcgcgcgcgt tatcttatta gaattcatcc cggagatcgc aatcccggtc      2400
ttgggcacct ttgcgttggt gagctatatc gcgaataaag tgctcacggt ccaaaccatc      2460
gataacgcgc tcagcaagcg taatgagaaa tgggacgagg tttataagta tatcgtgacc      2520
aactggttag caaaagtcaa tacgcagatc gatctcatcc gcaaaaaaat gaagaagcc      2580 ttggaaaatc aagcggaggc aaccaaagcc atcattaatt accagtataa ccaatatacc      2640
gaagaagaaa aaacaatat caacttcaat atcgatgatt tgagcagcaa actgaacgag      2700
agcattaaca aagcgatgat taacatcaac aagttcttga atcaatgcag cgtgagctat      2760
ctcatgaaca gcatgatccc gtatggcgtc aaacgcttgg aagattttga cgccagcctg      2820
aaagatgcgc tcctcaagta tatttatgac aaccgcggca ccctcattgg ccaggtggac      2880
cgcttgaagg ataaagtgaa caatacgctc agcacggata tcccgttcca gctgagcaag      2940
tacgtcgaca accagcgctt actgagcacc tttaccgagt atatcaagaa catcattaat      3000
accagcatcc tcaacttgcg ctatgagagc aatcacctga tcgacctcag ccgctacgcc      3060
agcaagatca acatcggcag caaggtcaat ttcgacccga tcgataagaa tcagatccaa      3120
ttgtttaacc tggaaagcag caagatcgag gttatcttga agaacgcgat tgtgtacaac      3180
agcatgtacg agaactttag cacgagcttc tggattcgta tcccgaagta tttcaatagc      3240
attagcctga ataacgaata taccattatc aactgcatgg aaaataatag cggctggaag      3300
gtgagcttaa attacggcga gatcatttgg accttacagg atacccaaga aatcaaacag      3360
cgcgtcgtct ttaagtatag ccagatgatc aacatcagcg attacatcaa ccgctggatc      3420
ttcgtgacca tcaccaataa tcgcttgaat aatagcaaga tttacatcaa tggtcgcttg      3480
attgatcaaa aaccgatcag caatctcggt aatatccatg ccagcaataa catcatgttt      3540
```

-continued

```
aagttagacg gttgccgcga tacccaccgc tatatctgga tcaagtattt taacttattt    3600
gataaggaac tcaacgaaaa ggaaattaaa gacttatatg acaatcagag caatagcggc    3660
atcctgaagg atttctgggg cgactacctg cagtacgata agccgtacta tatgttgaac    3720
ttgtatgacc cgaacaaata tgtcgatgtg aacaatgtgg gtattcgtgg ctatatgtac    3780
ttaaagggcc cgcgtggtag cgtgatgacc acgaatattt acttaaacag cagcttatac    3840
cgcggcacga agtttattat caagaagtat gccagcggca acaaggacaa tatcgtccgc    3900
aacaacgacc gtgtgtatat taacgtggtg gtgaagaata agagtaccg cttggccacg      3960 aatgcgagcc aggcgggcgt ggaaaaaatc ttgagcgcgt ggagatcccc ggacgtcggc    4020
aacctcagcc aggttgtggt gatgaagtct aaaaacgacc agggcatcac gaacaagtgc    4080
aaaatgaatt tgcaagataa caacggcaac gacatcggct ttattggttt tcaccagttc    4140
aataacatcg ccaaactcgt ggccagcaat tggtataacc gccaaattga acgcagcagc    4200
cgcacgctcg gctgtagctg ggagttcatc ccggtggacg atggctgggg cgagcgcccg    4260
ctcggagatc tggtgccacg cggttccgcg aattcgagct ccgtcgacaa gctttggagc    4320
cacccgcagt tcgaaaaata a                                               4341
```

<210> SEQ ID NO 12
<211> LENGTH: 100
<212> TYPE: PRT
<213> ORGANISM: Artificial Sequence
<220> FEATURE:
<223> OTHER INFORMATION: VPASA100 sequence

<400> SEQUENCE: 12

Val Pro Ala Ser Ala Val Pro Ala Ser Ala Val Pro Ala Ser Ala Val
1               5                   10                  15

Pro Ala Ser Ala Val Pro Ala Ser Ala Val Pro Ala Ser Ala Val Pro
                20                  25                  30

Ala Ser Ala Val Pro Ala Ser Ala Val Pro Ala Ser Ala Val Pro Ala
            35                  40                  45

Ser Ala Val Pro Ala Ser Ala Val Pro Ala Ser Ala Val Pro Ala Ser
        50                  55                  60

Ala Val Pro Ala Ser Ala Val Pro Ala Ser Ala Val Pro Ala Ser Ala
65                  70                  75                  80

Val Pro Ala Ser Ala Val Pro Ala Ser Ala Val Pro Ala Ser Ala Val
                85                  90                  95

Pro Ala Ser Ala
            100

<210> SEQ ID NO 13
<211> LENGTH: 100
<212> TYPE: PRT
<213> ORGANISM: Artificial Sequence
<220> FEATURE:
<223> OTHER INFORMATION: VAPSA100 sequence

<400> SEQUENCE: 13

Val Ala Pro Ser Ala Val Ala Pro Ser Ala Val Ala Pro Ser Ala Val
1               5                   10                  15

Ala Pro Ser Ala Val Ala Pro Ser Ala Val Ala Pro Ser Ala Val Ala
                20                  25                  30

Pro Ser Ala Val Ala Pro Ser Ala Val Ala Pro Ser Ala Val Ala Pro
            35                  40                  45

```
Ser Ala Val Ala Pro Ser Ala Val Ala Pro Ser Ala Val Ala Pro Ser
 50                  55                  60
Ala Val Ala Pro Ser Ala Val Ala Pro Ser Ala Val Ala Pro Ser Ala
 65                  70                  75                  80
Val Ala Pro Ser Ala Val Ala Pro Ser Ala Val Ala Pro Ser Ala Val
                 85                  90                  95
Ala Pro Ser Ala
            100

<210> SEQ ID NO 14
<211> LENGTH: 1443
<212> TYPE: PRT
<213> ORGANISM: Artificial Sequence
<220> FEATURE:
<223> OTHER INFORMATION: VPASA100 rBoNT/A: protein sequence

<400> SEQUENCE: 14

Met Gly Ser Ser His His His His His His Gly Ser Leu Val Pro Arg
1               5                   10                  15
Ser Val Pro Ala Ser Ala Val Pro Ala Ser Ala Val Pro Ala Ser Ala
                20                  25                  30
Val Pro Ala Ser Ala Val Pro Ala Ser Ala Val Pro Ala Ser Ala Val
                35                  40                  45
Pro Ala Ser Ala Val Pro Ala Ser Ala Val Pro Ala Ser Ala Val Pro
            50                  55                  60
Ala Ser Ala Val Pro Ala Ser Ala Val Pro Ala Ser Ala Val Pro Ala
 65                  70                  75                  80
Ser Ala Val Pro Ala Ser Ala Val Pro Ala Ser Ala Val Pro Ala Ser
                 85                  90                  95
Ala Val Pro Ala Ser Ala Val Pro Ala Ser Ala Val Pro Ala Ser Ala
                100                 105                 110
Val Pro Ala Ser Ala Pro Phe Val Asn Lys Gln Phe Asn Tyr Lys Asp
            115                 120                 125
Pro Val Asn Gly Val Asp Ile Ala Tyr Ile Lys Ile Pro Asn Ala Gly
        130                 135                 140
Gln Met Gln Pro Val Lys Ala Phe Lys Ile His Asn Lys Ile Trp Val
145                 150                 155                 160
Ile Pro Glu Arg Asp Thr Phe Thr Asn Pro Glu Glu Gly Asp Leu Asn
                165                 170                 175
Pro Pro Pro Glu Ala Lys Gln Val Pro Val Ser Tyr Tyr Asp Ser Thr
            180                 185                 190
Tyr Leu Ser Thr Asp Asn Glu Lys Asp Asn Tyr Leu Lys Gly Val Thr
        195                 200                 205
Lys Leu Phe Glu Arg Ile Tyr Ser Thr Asp Leu Gly Arg Met Leu Leu
    210                 215                 220
Thr Ser Ile Val Arg Gly Ile Pro Phe Trp Gly Gly Ser Thr Ile Asp
225                 230                 235                 240
Thr Glu Leu Lys Val Ile Asp Thr Asn Cys Ile Asn Val Ile Gln Pro
                245                 250                 255
Asp Gly Ser Tyr Arg Ser Glu Glu Leu Asn Leu Val Ile Ile Gly Pro
            260                 265                 270
Ser Ala Asp Ile Ile Gln Phe Glu Cys Lys Ser Phe Gly His Glu Val
        275                 280                 285
Leu Asn Leu Thr Arg Asn Gly Tyr Gly Ser Thr Gln Tyr Ile Arg Phe
    290                 295                 300
```

```
Ser Pro Asp Phe Thr Phe Gly Phe Glu Glu Ser Leu Glu Val Asp Thr
305                 310                 315                 320

Asn Pro Leu Leu Gly Ala Gly Lys Phe Ala Thr Asp Pro Ala Val Thr
            325                 330                 335

Leu Ala His Glu Leu Ile His Ala Gly His Arg Leu Tyr Gly Ile Ala
        340                 345                 350

Ile Asn Pro Asn Arg Val Phe Lys Val Asn Thr Asn Ala Tyr Tyr Glu
    355                 360                 365

Met Ser Gly Leu Glu Val Ser Phe Glu Glu Leu Arg Thr Phe Gly Gly
370                 375                 380

His Asp Ala Lys Phe Ile Asp Ser Leu Gln Glu Asn Glu Phe Arg Leu
385                 390                 395                 400

Tyr Tyr Tyr Asn Lys Phe Lys Asp Ile Ala Ser Thr Leu Asn Lys Ala
                405                 410                 415

Lys Ser Ile Val Gly Thr Thr Ala Ser Leu Gln Tyr Met Lys Asn Val
            420                 425                 430

Phe Lys Glu Lys Tyr Leu Leu Ser Glu Asp Thr Ser Gly Lys Phe Ser
        435                 440                 445

Val Asp Lys Leu Lys Phe Asp Lys Leu Tyr Lys Met Leu Thr Glu Ile
450                 455                 460

Tyr Thr Glu Asp Asn Phe Val Lys Phe Phe Lys Val Leu Asn Arg Lys
465                 470                 475                 480

Thr Tyr Leu Asn Phe Asp Lys Ala Val Phe Lys Ile Asn Ile Val Pro
                485                 490                 495

Lys Val Asn Tyr Thr Ile Tyr Asp Gly Phe Asn Leu Arg Asn Thr Asn
            500                 505                 510

Leu Ala Ala Asn Phe Asn Gly Gln Asn Thr Glu Ile Asn Asn Met Asn
        515                 520                 525

Phe Thr Lys Leu Lys Asn Phe Thr Gly Leu Phe Glu Phe Tyr Lys Leu
530                 535                 540

Leu Cys Val Arg Gly Ile Ile Thr Ser Lys Ala Gly Ala Gly Lys Ser
545                 550                 555                 560

Leu Val Pro Arg Gly Ser Ala Gly Ala Gly Ala Leu Asn Asp Leu Cys
                565                 570                 575

Ile Lys Val Asn Asn Trp Asp Leu Phe Phe Ser Pro Ser Glu Asp Asn
            580                 585                 590

Phe Thr Asn Asp Leu Asn Lys Gly Glu Glu Ile Thr Ser Asp Thr Asn
        595                 600                 605

Ile Glu Ala Ala Glu Glu Asn Ile Ser Leu Asp Leu Ile Gln Gln Tyr
610                 615                 620

Tyr Leu Thr Phe Asn Phe Asp Asn Glu Pro Glu Asn Ile Ser Ile Glu
625                 630                 635                 640

Asn Leu Ser Ser Asp Ile Ile Gly Gln Leu Glu Leu Met Pro Asn Ile
                645                 650                 655

Glu Arg Phe Pro Asn Gly Lys Lys Tyr Glu Leu Asp Lys Tyr Thr Met
            660                 665                 670

Phe His Tyr Leu Arg Ala Gln Glu Phe Glu His Gly Lys Ser Arg Ile
        675                 680                 685

Ala Leu Thr Asn Ser Val Asn Glu Ala Leu Leu Asn Pro Ser Arg Val
690                 695                 700

Tyr Thr Phe Phe Ser Ser Asp Tyr Val Lys Lys Val Asn Lys Ala Thr
705                 710                 715                 720

Glu Ala Ala Met Phe Leu Gly Trp Val Glu Gln Leu Val Tyr Asp Phe
```

```
                  725                 730                 735
Thr Asp Glu Thr Ser Glu Val Ser Thr Thr Asp Lys Ile Ala Asp Ile
                740                 745                 750

Thr Ile Ile Ile Pro Tyr Ile Gly Pro Ala Leu Asn Ile Gly Asn Met
                755                 760                 765

Leu Tyr Lys Asp Asp Phe Val Gly Ala Leu Ile Phe Ser Gly Ala Val
            770                 775                 780

Ile Leu Glu Phe Ile Pro Glu Ile Ala Ile Pro Val Leu Gly Thr
785                 790                 795                 800

Phe Ala Leu Val Ser Tyr Ile Ala Asn Lys Val Leu Thr Val Gln Thr
                805                 810                 815

Ile Asp Asn Ala Leu Ser Lys Arg Asn Glu Lys Trp Asp Glu Val Tyr
                820                 825                 830

Lys Tyr Ile Val Thr Asn Trp Leu Ala Lys Val Asn Thr Gln Ile Asp
                835                 840                 845

Leu Ile Arg Lys Lys Met Lys Glu Ala Leu Glu Asn Gln Ala Glu Ala
            850                 855                 860

Thr Lys Ala Ile Ile Asn Tyr Gln Tyr Asn Gln Tyr Thr Glu Glu Glu
865                 870                 875                 880

Lys Asn Asn Ile Asn Phe Asn Ile Asp Asp Leu Ser Ser Lys Leu Asn
                885                 890                 895

Glu Ser Ile Asn Lys Ala Met Ile Asn Ile Asn Lys Phe Leu Asn Gln
            900                 905                 910

Cys Ser Val Ser Tyr Leu Met Asn Ser Met Ile Pro Tyr Gly Val Lys
            915                 920                 925

Arg Leu Glu Asp Phe Asp Ala Ser Leu Lys Asp Ala Leu Leu Lys Tyr
            930                 935                 940

Ile Tyr Asp Asn Arg Gly Thr Leu Ile Gly Gln Val Asp Arg Leu Lys
945                 950                 955                 960

Asp Lys Val Asn Asn Thr Leu Ser Thr Asp Ile Pro Phe Gln Leu Ser
                965                 970                 975

Lys Tyr Val Asp Asn Gln Arg Leu Leu Ser Thr Phe Thr Glu Tyr Ile
            980                 985                 990

Lys Asn Ile Ile Asn Thr Ser Ile Leu Asn Leu Arg Tyr Glu Ser Asn
            995                1000                1005

His Leu Ile Asp Leu Ser Arg Tyr Ala Ser Lys Ile Asn Ile Gly
        1010                1015                1020

Ser Lys Val Asn Phe Asp Pro Ile Asp Lys Asn Gln Ile Gln Leu
        1025                1030                1035

Phe Asn Leu Glu Ser Ser Lys Ile Glu Val Ile Leu Lys Asn Ala
        1040                1045                1050

Ile Val Tyr Asn Ser Met Tyr Glu Asn Phe Ser Thr Ser Phe Trp
        1055                1060                1065

Ile Arg Ile Pro Lys Tyr Phe Asn Ser Ile Ser Leu Asn Asn Glu
        1070                1075                1080

Tyr Thr Ile Ile Asn Cys Met Glu Asn Asn Ser Gly Trp Lys Val
        1085                1090                1095

Ser Leu Asn Tyr Gly Glu Ile Ile Trp Thr Leu Gln Asp Thr Gln
        1100                1105                1110

Glu Ile Lys Gln Arg Val Val Phe Lys Tyr Ser Gln Met Ile Asn
        1115                1120                1125

Ile Ser Asp Tyr Ile Asn Arg Trp Ile Phe Val Thr Ile Thr Asn
        1130                1135                1140
```

```
Asn Arg Leu Asn Asn Ser Lys Ile Tyr Ile Asn Gly Arg Leu Ile
            1145                1150                1155

Asp Gln Lys Pro Ile Ser Asn Leu Gly Asn Ile His Ala Ser Asn
    1160                1165                1170

Asn Ile Met Phe Lys Leu Asp Gly Cys Arg Asp Thr His Arg Tyr
        1175                1180                1185

Ile Trp Ile Lys Tyr Phe Asn Leu Phe Asp Lys Glu Leu Asn Glu
    1190                1195                1200

Lys Glu Ile Lys Asp Leu Tyr Asp Asn Gln Ser Asn Ser Gly Ile
        1205                1210                1215

Leu Lys Asp Phe Trp Gly Asp Tyr Leu Gln Tyr Asp Lys Pro Tyr
    1220                1225                1230

Tyr Met Leu Asn Leu Tyr Asp Pro Asn Lys Tyr Val Asp Val Asn
        1235                1240                1245

Asn Val Gly Ile Arg Gly Tyr Met Tyr Leu Lys Gly Pro Arg Gly
    1250                1255                1260

Ser Val Met Thr Thr Asn Ile Tyr Leu Asn Ser Ser Leu Tyr Arg
        1265                1270                1275

Gly Thr Lys Phe Ile Ile Lys Lys Tyr Ala Ser Gly Asn Lys Asp
    1280                1285                1290

Asn Ile Val Arg Asn Asn Asp Arg Val Tyr Ile Asn Val Val Val
        1295                1300                1305

Lys Asn Lys Glu Tyr Arg Leu Ala Thr Asn Ala Ser Gln Ala Gly
    1310                1315                1320

Val Glu Lys Ile Leu Ser Ala Leu Glu Ile Pro Asp Val Gly Asn
        1325                1330                1335

Leu Ser Gln Val Val Val Met Lys Ser Lys Asn Asp Gln Gly Ile
    1340                1345                1350

Thr Asn Lys Cys Lys Met Asn Leu Gln Asp Asn Asn Gly Asn Asp
    1355                1360                1365

Ile Gly Phe Ile Gly Phe His Gln Phe Asn Asn Ile Ala Lys Leu
    1370                1375                1380

Val Ala Ser Asn Trp Tyr Asn Arg Gln Ile Glu Arg Ser Ser Arg
    1385                1390                1395

Thr Leu Gly Cys Ser Trp Glu Phe Ile Pro Val Asp Asp Gly Trp
    1400                1405                1410

Gly Glu Arg Pro Leu Gly Asp Leu Val Pro Arg Gly Ser Ala Asn
    1415                1420                1425

Ser Ser Ser Val Asp Lys Leu Trp Ser His Pro Gln Phe Glu Lys
    1430                1435                1440

<210> SEQ ID NO 15
<211> LENGTH: 1443
<212> TYPE: PRT
<213> ORGANISM: Artificial Sequence
<220> FEATURE:
<223> OTHER INFORMATION: VAPSA100 rBoNT/A: protein sequence

<400> SEQUENCE: 15

Met Gly Ser Ser His His His His His His Gly Ser Leu Val Pro Arg
1               5                   10                  15

Ser Val Ala Pro Ser Ala Val Ala Pro Ser Ala Val Ala Pro Ser Ala
            20                  25                  30

Val Ala Pro Ser Ala Val Ala Pro Ser Ala Val Ala Pro Ser Ala Val
        35                  40                  45
```

```
Ala Pro Ser Ala Val Ala Pro Ser Ala Val Ala Pro Ser Val Ala
    50                  55                  60
Pro Ser Ala Val Ala Pro Ser Ala Val Ala Pro Ser Ala Val Ala Pro
65                  70                  75                  80
Ser Ala Val Ala Pro Ser Ala Val Ala Pro Ser Ala Val Ala Pro Ser
                85                  90                  95
Ala Val Ala Pro Ser Ala Val Ala Pro Ser Ala Val Ala Pro Ser Ala
            100                 105                 110
Val Ala Pro Ser Ala Pro Phe Val Asn Lys Gln Phe Asn Tyr Lys Asp
        115                 120                 125
Pro Val Asn Gly Val Asp Ile Ala Tyr Ile Lys Ile Pro Asn Ala Gly
    130                 135                 140
Gln Met Gln Pro Val Lys Ala Phe Lys Ile His Asn Lys Ile Trp Val
145                 150                 155                 160
Ile Pro Glu Arg Asp Thr Phe Thr Asn Pro Glu Glu Gly Asp Leu Asn
                165                 170                 175
Pro Pro Pro Glu Ala Lys Gln Val Pro Val Ser Tyr Tyr Asp Ser Thr
            180                 185                 190
Tyr Leu Ser Thr Asp Asn Glu Lys Asp Asn Tyr Leu Lys Gly Val Thr
        195                 200                 205
Lys Leu Phe Glu Arg Ile Tyr Ser Thr Asp Leu Gly Arg Met Leu Leu
    210                 215                 220
Thr Ser Ile Val Arg Gly Ile Pro Phe Trp Gly Ser Thr Ile Asp
225                 230                 235                 240
Thr Glu Leu Lys Val Ile Asp Thr Asn Cys Ile Asn Val Ile Gln Pro
                245                 250                 255
Asp Gly Ser Tyr Arg Ser Glu Glu Leu Asn Leu Val Ile Ile Gly Pro
            260                 265                 270
Ser Ala Asp Ile Ile Gln Phe Glu Cys Lys Ser Phe Gly His Glu Val
        275                 280                 285
Leu Asn Leu Thr Arg Asn Gly Tyr Gly Ser Thr Gln Tyr Ile Arg Phe
    290                 295                 300
Ser Pro Asp Phe Thr Phe Gly Phe Glu Glu Ser Leu Glu Val Asp Thr
305                 310                 315                 320
Asn Pro Leu Leu Gly Ala Gly Lys Phe Ala Thr Asp Pro Ala Val Thr
                325                 330                 335
Leu Ala His Glu Leu Ile His Ala Gly His Arg Leu Tyr Gly Ile Ala
            340                 345                 350
Ile Asn Pro Asn Arg Val Phe Lys Val Asn Thr Asn Ala Tyr Tyr Glu
        355                 360                 365
Met Ser Gly Leu Glu Val Ser Phe Glu Glu Leu Arg Thr Phe Gly Gly
    370                 375                 380
His Asp Ala Lys Phe Ile Asp Ser Leu Gln Glu Asn Glu Phe Arg Leu
385                 390                 395                 400
Tyr Tyr Tyr Asn Lys Phe Lys Asp Ile Ala Ser Thr Leu Asn Lys Ala
                405                 410                 415
Lys Ser Ile Val Gly Thr Thr Ala Ser Leu Gln Tyr Met Lys Asn Val
            420                 425                 430
Phe Lys Glu Lys Tyr Leu Leu Ser Glu Asp Thr Ser Gly Lys Phe Ser
        435                 440                 445
Val Asp Lys Leu Lys Phe Asp Lys Leu Tyr Lys Met Leu Thr Glu Ile
    450                 455                 460
```

```
Tyr Thr Glu Asp Asn Phe Val Lys Phe Phe Lys Val Leu Asn Arg Lys
465                 470                 475                 480

Thr Tyr Leu Asn Phe Asp Lys Ala Val Phe Lys Ile Asn Ile Val Pro
            485                 490                 495

Lys Val Asn Tyr Thr Ile Tyr Asp Gly Phe Asn Leu Arg Asn Thr Asn
        500                 505                 510

Leu Ala Ala Asn Phe Asn Gly Gln Asn Thr Glu Ile Asn Asn Met Asn
    515                 520                 525

Phe Thr Lys Leu Lys Asn Phe Thr Gly Leu Phe Glu Phe Tyr Lys Leu
530                 535                 540

Leu Cys Val Arg Gly Ile Ile Thr Ser Lys Ala Gly Ala Gly Lys Ser
545                 550                 555                 560

Leu Val Pro Arg Gly Ser Ala Gly Ala Leu Asn Asp Leu Cys
            565                 570                 575

Ile Lys Val Asn Asn Trp Asp Leu Phe Phe Ser Pro Ser Glu Asp Asn
                580                 585                 590

Phe Thr Asn Asp Leu Asn Lys Gly Glu Ile Thr Ser Asp Thr Asn
    595                 600                 605

Ile Glu Ala Ala Glu Glu Asn Ile Ser Leu Asp Leu Ile Gln Gln Tyr
610                 615                 620

Tyr Leu Thr Phe Asn Phe Asp Asn Glu Pro Glu Asn Ile Ser Ile Glu
625                 630                 635                 640

Asn Leu Ser Ser Asp Ile Ile Gly Gln Leu Glu Leu Met Pro Asn Ile
            645                 650                 655

Glu Arg Phe Pro Asn Gly Lys Lys Tyr Glu Leu Asp Lys Tyr Thr Met
            660                 665                 670

Phe His Tyr Leu Arg Ala Gln Glu Phe Glu His Gly Lys Ser Arg Ile
    675                 680                 685

Ala Leu Thr Asn Ser Val Asn Glu Ala Leu Leu Asn Pro Ser Arg Val
    690                 695                 700

Tyr Thr Phe Phe Ser Ser Asp Tyr Val Lys Lys Val Asn Lys Ala Thr
705                 710                 715                 720

Glu Ala Ala Met Phe Leu Gly Trp Val Glu Gln Leu Val Tyr Asp Phe
            725                 730                 735

Thr Asp Glu Thr Ser Glu Val Ser Thr Thr Asp Lys Ile Ala Asp Ile
        740                 745                 750

Thr Ile Ile Ile Pro Tyr Ile Gly Pro Ala Leu Asn Ile Gly Asn Met
    755                 760                 765

Leu Tyr Lys Asp Asp Phe Val Gly Ala Leu Ile Phe Ser Gly Ala Val
    770                 775                 780

Ile Leu Leu Glu Phe Ile Pro Glu Ile Ala Ile Pro Val Leu Gly Thr
785                 790                 795                 800

Phe Ala Leu Val Ser Tyr Ile Ala Asn Lys Val Leu Thr Val Gln Thr
            805                 810                 815

Ile Asp Asn Ala Leu Ser Lys Arg Asn Glu Lys Trp Asp Glu Val Tyr
        820                 825                 830

Lys Tyr Ile Val Thr Asn Trp Leu Ala Lys Val Asn Thr Gln Ile Asp
    835                 840                 845

Leu Ile Arg Lys Lys Met Lys Glu Ala Leu Glu Asn Gln Ala Glu Ala
    850                 855                 860

Thr Lys Ala Ile Ile Asn Tyr Gln Tyr Asn Gln Tyr Thr Glu Glu Glu
865                 870                 875                 880

Lys Asn Asn Ile Asn Phe Asn Ile Asp Asp Leu Ser Ser Lys Leu Asn
```

-continued

```
                885                 890                 895
Glu Ser Ile Asn Lys Ala Met Ile Asn Ile Asn Lys Phe Leu Asn Gln
                900                 905                 910

Cys Ser Val Ser Tyr Leu Met Asn Ser Met Ile Pro Tyr Gly Val Lys
                915                 920                 925

Arg Leu Glu Asp Phe Asp Ala Ser Leu Lys Asp Ala Leu Leu Lys Tyr
                930                 935                 940

Ile Tyr Asp Asn Arg Gly Thr Leu Ile Gly Gln Val Asp Arg Leu Lys
945                 950                 955                 960

Asp Lys Val Asn Asn Thr Leu Ser Thr Asp Ile Pro Phe Gln Leu Ser
                965                 970                 975

Lys Tyr Val Asp Asn Gln Arg Leu Leu Ser Thr Phe Thr Glu Tyr Ile
                980                 985                 990

Lys Asn Ile Ile Asn Thr Ser Ile Leu Asn Leu Arg Tyr Glu Ser Asn
                995                 1000                1005

His Leu Ile Asp Leu Ser Arg Tyr Ala Ser Lys Ile Asn Ile Gly
    1010                1015                1020

Ser Lys Val Asn Phe Asp Pro Ile Asp Lys Asn Gln Ile Gln Leu
    1025                1030                1035

Phe Asn Leu Glu Ser Ser Lys Ile Glu Val Ile Leu Lys Asn Ala
    1040                1045                1050

Ile Val Tyr Asn Ser Met Tyr Glu Asn Phe Ser Thr Ser Phe Trp
    1055                1060                1065

Ile Arg Ile Pro Lys Tyr Phe Asn Ser Ile Ser Leu Asn Asn Glu
    1070                1075                1080

Tyr Thr Ile Ile Asn Cys Met Glu Asn Asn Ser Gly Trp Lys Val
    1085                1090                1095

Ser Leu Asn Tyr Gly Glu Ile Ile Trp Thr Leu Gln Asp Thr Gln
    1100                1105                1110

Glu Ile Lys Gln Arg Val Val Phe Lys Tyr Ser Gln Met Ile Asn
    1115                1120                1125

Ile Ser Asp Tyr Ile Asn Arg Trp Ile Phe Val Thr Ile Thr Asn
    1130                1135                1140

Asn Arg Leu Asn Asn Ser Lys Ile Tyr Ile Asn Gly Arg Leu Ile
    1145                1150                1155

Asp Gln Lys Pro Ile Ser Asn Leu Gly Asn Ile His Ala Ser Asn
    1160                1165                1170

Asn Ile Met Phe Lys Leu Asp Gly Cys Arg Asp Thr His Arg Tyr
    1175                1180                1185

Ile Trp Ile Lys Tyr Phe Asn Leu Phe Asp Lys Glu Leu Asn Glu
    1190                1195                1200

Lys Glu Ile Lys Asp Leu Tyr Asp Asn Gln Ser Asn Ser Gly Ile
    1205                1210                1215

Leu Lys Asp Phe Trp Gly Asp Tyr Leu Gln Tyr Asp Lys Pro Tyr
    1220                1225                1230

Tyr Met Leu Asn Leu Tyr Asp Pro Asn Lys Tyr Val Asp Val Asn
    1235                1240                1245

Asn Val Gly Ile Arg Gly Tyr Met Tyr Leu Lys Gly Pro Arg Gly
    1250                1255                1260

Ser Val Met Thr Thr Asn Ile Tyr Leu Asn Ser Ser Leu Tyr Arg
    1265                1270                1275

Gly Thr Lys Phe Ile Ile Lys Lys Tyr Ala Ser Gly Asn Lys Asp
    1280                1285                1290
```

```
Asn Ile Val Arg Asn Asn Asp Arg Val Tyr Ile Asn Val Val Val
    1295            1300            1305

Lys Asn Lys Glu Tyr Arg Leu Ala Thr Asn Ala Ser Gln Ala Gly
    1310            1315            1320

Val Glu Lys Ile Leu Ser Ala Leu Glu Ile Pro Asp Val Gly Asn
    1325            1330            1335

Leu Ser Gln Val Val Val Met Lys Ser Lys Asn Asp Gln Gly Ile
    1340            1345            1350

Thr Asn Lys Cys Lys Met Asn Leu Gln Asp Asn Asn Gly Asn Asp
    1355            1360            1365

Ile Gly Phe Ile Gly Phe His Gln Phe Asn Asn Ile Ala Lys Leu
    1370            1375            1380

Val Ala Ser Asn Trp Tyr Asn Arg Gln Ile Glu Arg Ser Ser Arg
    1385            1390            1395

Thr Leu Gly Cys Ser Trp Glu Phe Ile Pro Val Asp Asp Gly Trp
    1400            1405            1410

Gly Glu Arg Pro Leu Gly Asp Leu Val Pro Arg Gly Ser Ala Asn
    1415            1420            1425

Ser Ser Ser Val Asp Lys Leu Trp Ser His Pro Gln Phe Glu Lys
    1430            1435            1440
```

RECOMBINANT CLOSTRIDIAL NEUROTOXINS WITH INCREASED DURATION OF EFFECT

CROSS-REFERENCE TO RELATED APPLICATIONS

This application is a National Stage entry of International Application No. PCT/EP2016/000962, filed Jun. 10, 2016, which claims priority to European Patent Application No. 15001733.3, filed Jun. 11, 2015.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_3000027-220000_ST25.txt" created on 4 Dec. 2017, and 67,616 bytes in size) is submitted concurrently with the instant application, and the entire contents of the Sequence Listing are incorporated herein by reference.

BACKGROUND

Field of the Invention

This invention relates to novel recombinant clostridial neurotoxins exhibiting increased duration of effect and to methods for the manufacture of such recombinant clostridial neurotoxins. These novel recombinant clostridial neurotoxins comprise a random coil domain, and the methods comprise the steps of inserting a nucleic acid sequence coding for a random coil domain into a nucleic acid sequence coding for a parental clostridial neurotoxin and expression of the recombinant nucleic acid sequence comprising the random coil domain-coding sequence in a host cell. The invention further relates to novel recombinant single-chain precursor clostridial neurotoxins used in such methods, nucleic acid sequences encoding such recombinant single-chain precursor clostridial neurotoxins, and pharmaceutical compositions comprising the recombinant clostridial neurotoxin with increased duration of effect.

DESCRIPTION OF RELATED ART

*Clostridium* is a genus of anaerobe gram-positive bacteria, belonging to the *Firmicutes*. *Clostridium* consists of around 100 species that include common free-living bacteria as well as important pathogens, such as *Clostridium botulinum* and *Clostridium tetani*. Both species produce neurotoxins, botulinum toxin and tetanus toxin, respectively. These neurotoxins are potent inhibitors of calcium-dependent neurotransmitter secretion of neuronal cells and are among the strongest toxins known to man. The lethal dose in humans lies between 0.1 ng and 1 ng per kilogram of body weight.

Oral ingestion of botulinum toxin via contaminated food or generation of botulinum toxin in wounds can cause botulism, which is characterised by paralysis of various muscles. Paralysis of the breathing muscles can cause death of the affected individual.

Although both botulinum neurotoxin (BoNT) and tetanus neurotoxin (TxNT) function via a similar initial physiological mechanism of action, inhibiting neurotransmitter release from the axon of the affected neuron into the synapse, they differ in their clinical response. While the botulinum toxin acts at the neuromuscular junction and other cholinergic synapses in the peripheral nervous system, inhibiting the release of the neurotransmitter acetylcholine and thereby causing flaccid paralysis, the tetanus toxin acts mainly in the central nervous system, preventing the release of the inhibitory neurotransmitters GABA (gamma-aminobutyric acid) and glycine by degrading the protein synaptobrevin. The consequent overactivity in the muscles results in generalized contractions of the agonist and antagonist musculature, termed a tetanic spasm (rigid paralysis).

While the tetanus neurotoxin exists in one immunologically distinct type, the botulinum neurotoxins are known to occur in seven different immunogenic types, termed BoNT/A through BoNT/G. Most *Clostridium botulinum* strains produce one type of neurotoxin, but strains producing multiple toxins have also been described.

Botulinum and tetanus neurotoxins have highly homologous amino acid sequences and show a similar domain structure. Their biologically active form comprises two peptide chains, a light chain of about 50 kDa and a heavy chain of about 100 kDa, linked by a disulfide bond. A linker or loop region, whose length varies among different clostridial toxins, is located between the two cysteine residues forming the disulfide bond. This loop region is proteolytically cleaved by an unknown clostridial endoprotease to obtain the biologically active toxin.

The molecular mechanism of intoxication by TxNT and BoNT appears to be similar as well: entry into the target neuron is mediated by binding of the C-terminal part of the heavy chain to a specific cell surface receptor; the toxin is then taken up by receptor-mediated endocytosis. The low pH in the so formed endosome then triggers a conformational change in the clostridial toxin which allows it to embed itself in the endosomal membrane and to translocate through the endosomal membrane into the cytoplasm, where the disulfide bond joining the heavy and the light chain is reduced. The light chain can then selectively cleave so called SNARE-proteins, which are essential for different steps of neurotransmitter release into the synaptic cleft, e.g. recognition, docking and fusion of neurotransmitter-containing vesicles with the plasma membrane. TxNT, BoNT/B, BoNT/D, BoNT/F, and BoNT/G cause proteolytic cleavage of synaptobrevin or VAMP (vesicle-associated membrane protein), BoNT/A and BoNT/E cleave the plasma membrane-associated protein SNAP-25, and BoNT/C cleaves the integral plasma membrane protein syntaxin and SNAP-25.

Clostridial neurotoxins display variable durations of action that are serotype specific. The clinical therapeutic effect of BoNT/A lasts approximately 3 months for neuromuscular disorders and 6 to 12 months for hyperhidrosis. The effects of BoNT/E, on the other hand, last less than 4 weeks. The longer lasting therapeutic effect of BoNT/A makes it preferable for clinical use compared to the other serotypes, for example serotypes B, $C_1$, D, E, F, and G. One possible explanation for the divergent durations of action might be the distinct subcellular localizations of BoNT serotypes. The protease domain of BoNT/A light chain localizes in a punctate manner to the plasma membrane of neuronal cells, co-localizing with its substrate SNAP-25. In contrast, the short-duration BoNT/E serotype is cytoplasmic. Membrane association might protect BoNT/A from cytosolic degradation mechanisms allowing for prolonged persistence of BoNT/A in the neuronal cell.

In *Clostridium botulinum*, the botulinum toxin is formed as a protein complex comprising the neurotoxic component and non-toxic proteins. The accessory proteins embed the neurotoxic component thereby protecting it from degradation by digestive enzymes in the gastrointestinal tract. Thus, botulinum neurotoxins of most serotypes are orally toxic. Complexes with, for example, 450 kDa or with 900 kDa are obtainable from cultures of *Clostridium botulinum.*

In recent years, botulinum neurotoxins have been used as therapeutic agents in the treatment of dystonias and spasms. Preparations comprising botulinum toxin complexes are commercially available, e.g. from Ipsen Ltd (Dysport®) or Allergan Inc. (Botox®). A high purity neurotoxic component, free of any complexing proteins, is for example available from Merz Pharmaceuticals GmbH, Frankfurt (Xeomin®).

Clostridial neurotoxins are usually injected into the affected muscle tissue, bringing the agent close to the neuromuscular end plate, i.e. close to the cellular receptor mediating its uptake into the nerve cell controlling said affected muscle. Various degrees of neurotoxin spread have been observed. The neurotoxin spread is thought to depend on the injected amount and the particular neurotoxin preparation. It can result in adverse side effects such as paralysis in nearby muscle tissue, which can largely be avoided by reducing the injected doses to the therapeutically relevant level. Overdosing can also trigger the immune system to generate neutralizing antibodies that inactivate the neurotoxin preventing it from relieving the involuntary muscle activity. Immunologic tolerance to botulinum toxin has been shown to correlate with cumulative doses.

At present, clostridial neurotoxins are still predominantly produced by fermentation processes using appropriate *Clostridium* strains. However, industrial production of clostridial neurotoxin from anaerobic *Clostridium* culture is a cumbersome and time-consuming process. Due to the high toxicity of the final product, the procedure must be performed under strict containment. During the fermentation process, the single-chain precursors are proteolytically cleaved by an unknown clostridial protease to obtain the biologically active di-chain clostridial neurotoxin. The degree of neurotoxin activation by proteolytic cleavage varies between different strains and neurotoxin serotypes, which is a major consideration for the manufacture due to the requirement of neurotoxin preparations with a well-defined biological activity. Furthermore, during fermentation processes using *Clostridium* strains the clostridial neurotoxins are produced as protein complexes, in which the neurotoxic component is embedded by accessory proteins. These accessory proteins have no beneficial effect on biological activity or duration of effect. They can however trigger an immune reaction in the patient, resulting in immunity against the clostridial neurotoxin. Manufacture of recombinant clostridial neurotoxins, which are not embedded by auxiliary proteins, might therefore be advantageous.

Methods for the recombinant expression of clostridial neurotoxins in *E. coli* are well known in the art (see, for example, WO 00/12728, WO 01/14570, or WO 2006/076902). Furthermore, clostridial neurotoxins have been expressed in eukaryotic expression systems, such as in *Pichia pastoris, Pichia methanolica, Saccharomyces cerevisiae*, insect cells and mammalian cells (see WO 2006/017749).

Recombinant clostridial neurotoxins may be expressed as single-chain precursors, which subsequently have to be proteolytically cleaved to obtain the final biologically active clostridial neurotoxin. Thus, clostridial neurotoxins may be expressed in high yield in rapidly-growing bacteria as relatively non-toxic single-chain polypeptides.

Furthermore, it might be advantageous to modify clostridial neurotoxin characteristics regarding biological activity, cell specificity, antigenic potential and duration of effect by genetic engineering to obtain recombinant neurotoxins with new therapeutic properties in specific clinical areas. Genetic modification of clostridial neurotoxins might allow altering the mode of action or expanding the range of therapeutic targets.

WO 96/39166 discloses analogues of botulinum toxin comprising amino acid residues which are more resistant to degradation in neuromuscular tissue.

Patent family based on WO 02/08268 (including family member U.S. Pat. No. 6,903,187) discloses a clostridial neurotoxin comprising a structural modification selected from addition or deletion of a leucine-based motif, which alters the biological persistence of the neurotoxin (see also: Fernández-Salas et al., Proc. Natl. Acad. Sci. U.S.A. 101 (2004) 3208-3213; Wang et al., J. Biol. Chem. 286 (2011) 6375-6385). Fernández-Sales et al. initially hypothesized that the increased persistence was due to the membrane-binding properties of the dileucine motif (see Fernández-Salas et al., loc. cit., p. 3211 and 3213). Wang et al. mention this membrane theory (see Wang et al., loc. cit., p. 6376, left column, last full paragraph, and p. 6383, first full paragraph of "Discussion"), but favor an alternative theory: the protection from degradation by proteolysis (see Wang et al., loc. cit., p. 6384, left column, lines 27ff).

US 2002/0127247 describes clostridial neurotoxins comprising modifications in secondary modification sites and exhibiting altered biological persistence.

Botulinum toxin variants exhibiting longer biological half lives in neuromuscular tissue than naturally occurring botulinum toxins would be advantageous in order to reduce administration frequency and the incidence of neutralising antibody generation since immunologic tolerance to botulinum toxin is correlated with cumulative doses.

Furthermore, BoNT serotypes naturally exhibiting a short duration of action could potentially be effectively used in clinical applications, if their biological persistence could be enhanced. Modified BoNT/E with an increased duration of action could potentially be used in patients exhibiting an immune reaction against BoNT/A. Moreover, BoNT/E was shown to induce a more severe block of pain mediator release from sensory neurons than BoNT/A. In clinical applications where BoNT/A provides only partial pain relief or in just a subset of patients, such as in the treatment of headaches, or where BoNT/E has been found to be more effective than BoNT/A but gives only short-term therapy, such as in the treatment of epilepsy, BoNT/E with an increased duration of effect might prove useful.

There is a strong demand to produce clostridial neurotoxins with an increased duration of effect, in order to allow for reduction of administration frequency and exploitation of the therapeutic potential of BoNT serotypes, which have so far been considered impractical for clinical application due to the short half-life of the respective clinically relevant effect. Ideally, the duration of effect of a particular clostridial neurotoxin could be adjusted in a tailor-made fashion in order to address any particular features and demands of a given indication, such as the amount of neurotoxin being administered, frequency of administration etc. To date, such aspects have not been solved satisfactorily.

OBJECTS OF THE INVENTION

It was an object of the invention to provide recombinant clostridial neurotoxins exhibiting an increased duration of effect and to establish a reliable and accurate method for manufacturing and obtaining such recombinant clostridial neurotoxins. Such a method and novel precursor clostridial neurotoxins used in such methods would serve to satisfy the great need for recombinant clostridial neurotoxins exhibiting an increased duration of effect.

SUMMARY OF THE INVENTION

The naturally occurring botulinum toxin serotypes display highly divergent durations of effect, probably due to their distinct subcellular localization. BoNT/A exhibiting the longest persistence was shown to localize in the vicinity of the plasma membrane of neuronal cells, whereas the short-duration BoNT/E serotype is cytosolic. However, additional factors such as degradation, diffusion, and/or translocation rates might have a decisive impact on the differences in the duration of effect for the individual botulinum toxin serotypes.

So far, no generally applicable method for modifying clostridial neurotoxins in order to increase their duration of effect is available. Surprisingly, it has been found that recombinant clostridial neurotoxins having such effects can be obtained by cloning a sequence encoding a random coil domain into a gene encoding a parental clostridial neurotoxin, and by subsequent heterologous expression of the generated construct in recombinant host cells.

Thus, in one aspect, the present invention relates to recombinant clostridial neurotoxin comprising a random coil domain.

In a particular embodiment, the invention relates to a recombinant clostridial neurotoxin comprising a random coil domain, wherein (i) said random coil domain consists of the amino acid sequence $(Xaa)_x-[(P,A,S)_y-(Xaa)-]_z(P,A,S)_y-(Xaa)_x$, wherein Xaa is an amino acid residue independently selected from any naturally occurring amino acid residue, provided that at least one Xaa in $[(P,A,S)_y-(Xaa)-]_z$ is different from an alanine, serine or proline residue; particularly wherein Xaa is valine; (P,A,S) represents an amino acid residue independently selected from an alanine (A), a serine (S) and a proline (P) residue; x is a number independently selected from 0 and 1; y is a number independently selected from 3 and 4; and z is 9 or more, particularly z is a number between 9 and 750.

In another aspect, the present invention relates to a pharmaceutical composition comprising the recombinant clostridial neurotoxin of the present invention.

In yet another aspect, the present invention relates to the use of the composition of the present invention for cosmetic treatment.

In another aspect, the present invention relates to a method for the generation of the recombinant clostridial neurotoxin of the present invention, comprising the step of obtaining a recombinant nucleic acid sequence encoding a recombinant single-chain precursor clostridial neurotoxin by the insertion of a nucleic acid sequence encoding said random coil domain, in particular a random coil domain according to the present invention, into a nucleic acid sequence encoding a parental clostridial neurotoxin.

In another aspect, the present invention relates to a recombinant single-chain precursor clostridial neurotoxin comprising a random coil domain, in particular a random coil domain according to the present invention.

In another aspect, the present invention relates to a nucleic acid sequence encoding the recombinant single-chain precursor clostridial neurotoxin of the present invention.

In another aspect, the present invention relates to a method for obtaining the nucleic acid sequence of the present invention, comprising the step of inserting a nucleic acid sequence encoding a random coil domain, in particular a random coil domain according to the present invention, into a nucleic acid sequence encoding a parental clostridial neurotoxin.

In another aspect, the present invention relates to a vector comprising the nucleic acid sequence of the present invention, or the nucleic acid sequence obtainable by the method of the present invention.

In another aspect, the present invention relates to a recombinant host cell comprising the nucleic acid sequence of the present invention, the nucleic acid sequence obtainable by the method of the present invention, or the vector of the present invention.

In another aspect, the present invention relates to a method for producing the recombinant single-chain precursor clostridial neurotoxin of the present invention, comprising the step of expressing the nucleic acid sequence of the present invention, or the nucleic acid sequence obtainable by the method of the present invention, or the vector of the present invention in a recombinant host cell, or cultivating the recombinant host cell of the present invention under conditions that result in the expression of said nucleic acid sequence.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4: Mouse running assay with PAS100-rBoNT/A: ■: PAS100-rBoNT/A, ●: mean of Standard (54 assays) from Xeomin 81208 (0.6U)

FIG. 5: Mouse running assay with VPASA100 rBoNT/A: ●: (2) VPASA100 rBoNT/A; ●: mean of Standard (54 assays) from Xeomin 81208 (0.6U)

DETAILED DESCRIPTION OF A PREFERRED EMBODIMENT

Figure 1:
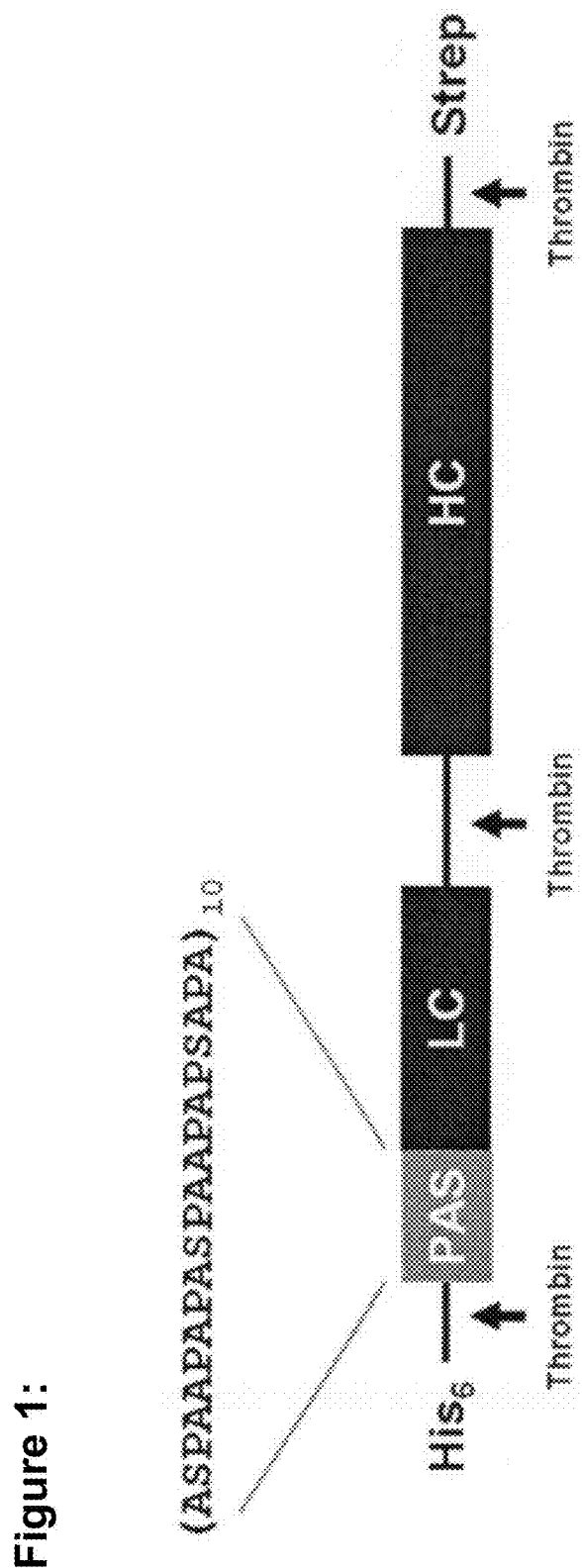
FIG. 1: Schematic Presentation of PASylated Botulinum Toxin A (PAS-rBoNT/A).

The present invention may be understood more readily by reference to the following detailed description of the invention and the examples included therein.

In one aspect, the present invention relates to a recombinant clostridial neurotoxin comprising a random coil domain.

In the context of the present invention, the term "clostridial neurotoxin" refers to a natural neurotoxin obtainable from bacteria of the class *Clostridia*, including Clostridium tetani and Clostridium botulinum, or to a neurotoxin obtainable from alternative sources, including from recombinant technologies or from genetic or chemical modification. Particularly, the clostridial neurotoxins have endopeptidase activity.

Clostridial neurotoxins are produced as single-chain precursors that are proteolytically cleaved by an unknown clostridial endoprotease within the loop region to obtain the biologically active disulfide-linked di-chain form of the neurotoxin, which comprises two chain elements, a functionally active light chain and a functionally active heavy chain, where one end of the light chain is linked to one end of the heavy chain not via a peptide bond, but via a disulfide bond.

In the context of the present invention, the term "clostridial neurotoxin light chain" refers to that part of a clostridial neurotoxin that comprises an endopeptidase activity responsible for cleaving one or more proteins that is/are part of the so-called SNARE-complex involved in the process resulting in the release of neurotransmitter into the synaptic cleft: In naturally occurring clostridial neurotoxins, the light chain has a molecular weight of approx. 50 kDa.

In the context of the present invention, the term "clostridial neurotoxin heavy chain" refers to that part of a clostridial neurotoxin that is responsible for entry of the neurotoxin into the neuronal cell: In naturally occurring clostridial neurotoxins, the heavy chain has a molecular weight of approx. 100 kDa.

In the context of the present invention, the term "functionally active clostridial neurotoxin chain" refers to a recombinant clostridial neurotoxin chain able to perform the biological functions of a naturally occurring Clostridium botulinum neurotoxin chain to at least about 50%, particularly to at least about 60%, to at least about 70%, to at least about 80%, and most particularly to at least about 90%, where the biological functions of clostridial neurotoxin chains include, but are not limited to, binding of the heavy chain to the neuronal cell, entry of the neurotoxin into a neuronal cell, release of the light chain from the di-chain neurotoxin, and endopeptidase activity of the light chain. Methods for determining a neurotoxic activity can be found, for example, in WO 95/32738, which describes the reconstitution of separately obtained light and heavy chains of tetanus toxin and botulinum toxin.

In the context of the present invention, the term "about" or "approximately" means within 20%, alternatively within 10%, including within 5% of a given value or range. Alternatively, especially in biological systems, the term "about" means within about a log (i.e. an order of magnitude), including within a factor of two of a given value.

In the context of the present invention, the term "recombinant clostridial neurotoxin" refers to a composition comprising a clostridial neurotoxin that is obtained by expression of the neurotoxin in a heterologous cell such as E. coli, and including, but not limited to, the raw material obtained from a fermentation process (supernatant, composition after cell lysis), a fraction comprising a clostridial neurotoxin obtained from separating the ingredients of such a raw material in a purification process, an isolated and essentially pure protein, and a formulation for pharmaceutical and/or aesthetic use comprising a clostridial neurotoxin and additionally pharmaceutically acceptable solvents and/or excipients.

In the context of the present invention, the term "recombinant clostridial neurotoxin" further refers to a clostridial neurotoxin based on a parental clostridial neurotoxin additionally comprising a heterologous random coil domain, i.e. a random coil domain that is not naturally occurring in said parental clostridial neurotoxin, in particular a synthetic random coil domain, or a random coil domain from a species other than Clostridium botulinum, in particular a random coil domain from a human protein.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components, or groups thereof. The term "comprising" thus includes the more restrictive terms "consisting of" and "consisting essentially of".

In the context of the present invention, the term "random coil domain" refers to a protein segment, which is essentially lacking a secondary structure. Random coil domains can be detected using a variety of methods, including spectroscopic methods such as circular dichroism or nuclear magnetic resonance (NMR) methods, including multidimensional NMR experiments, or crystallographic structure determinations.

In particular embodiments, said random coil domain consists of the amino acid sequence $(Xaa)_x\text{-}[(P,A,S)_y\text{-}(Xaa)\text{-}]_z(P,A,S)_y\text{-}(Xaa)_x$, wherein Xaa is an amino acid residue independently selected from any naturally occurring amino acid residue, provided that at least one Xaa in $[(P,A,S)_y\text{-}(Xaa)\text{-}]_z$ is different from an alanine, serine or proline residue; particularly wherein Xaa is valine; (P,A,S) represents an amino acid residue independently selected from an alanine (A), a serine (S) and a proline (P) residue; x is a number independently selected from 0 and 1; y is a number independently selected from 3 and 4; and z is 9 or more, particularly z is a number between 9 and 750.

In particular such embodiments, y is 3, and z is 11 or more, particularly z is a number between 11 and 749, more particularly between 14 and 124, more particularly between 16 and 67, more particularly between 19 and 59, more particularly between 21 and 54, or more particularly 23, 24, or 25, or 35, 36, or 37, or 48, 49, or 50. In other particular such embodiments, y is 4, and z is 9 or more, particularly z is a number between 9 and 599, more particularly between 11 and 99, more particularly between 13 and 51, more particularly between 15 and 47, more particularly between 17 and 43, or more particularly 18, 19, or 20, or 28, 29, or 30, or 38, 39, or 40.

The so-called "PAS" sequences (see, for example, Schlapschy et al., Protein Engineering, Design and Selection 26 (2013) 489-501; EP 2 369 005; WO 2011/144756) have been developed in order to extend the plasma half-life of pharmaceutically active proteins. It is argued that the genetic fusion with such conformationally disordered polypeptide sequences provides a simple way to attach a solvated random chain with large hydrodynamic volume to the fusion partner, for example a protein of biopharmaceutical interest, so that the size of the resulting fusion protein is significantly increased, and that by these means the typically rapid clearance of the biologically active component via kidney filtration is retarded by one to two orders of magnitude.

Surprisingly, it has been found that attachment of a random coil domain based on a PAS domain, which comprises further amino acid residues other than P, A, or S, particularly valine, is also able to extend the duration of effect of a protein that is active intracellularly, particularly since plasma half-life of botulinum toxins has so far not been regarded as being of critical importance for their duration of effect. The extension of duration is furthermore particularly surprising, since it has been argued that macromolecular side chains such as PAS(Xaa) sequences or polyethylene glycol-based sequences prevent the cellular uptake, so that this way of intravasal protein stabilization could only be applied to proteins for therapeutic intervention with cell surface markers or receptors (A. Weber, Inhibierung von Stat5 in Tumoren durch RNA-Interferenz and spezifische Interaktion eines Peptidaptamer-Konstruktes mit der DNA-Bindedomane, PhD thesis, Johann-Wolfgang-Goethe Universität, Frankfurt am Main (Germany) 2013, p. 220, final full sentence).

In particular embodiments, said random coil domain consists of alanine, serine and proline residues.

In particular embodiments, said random coil domain comprises a plurality of amino acid repeats, wherein said repeats consist of Ala, Ser, and Pro residues and wherein no more than six consecutive amino acid residues are identical.

In particular embodiments, said random coil domain comprises an amino acid sequence consisting of at least 50 amino acid residues forming random coil conformation, particularly between 50 and 3000 amino acid residues, more particularly between 60 and 500 amino acid residues, more particularly between 70 and 260 amino acid residues, more particularly between 80 and 240 amino acid residues, more particularly between 90 and 220 amino acid residues, particularly 100 amino acid residues, 150 amino acid residues, or 200 amino acid residues.

In particular embodiments, the proline residues comprised in said random coil domain constitute more than 4% and less than 40% of the amino acids of said random coil domain.

In particular embodiments, said random coil domain comprises at least one amino acid sequence selected from the group consisting of: $(VPASA)_{20}$ (SEQ ID NO: 12) and $(VAPSA)_{20}$ (SEQ ID NO: 13).

In particular other embodiments, at least 20% of said amino acid residues (Xaa) are different from alanine (A), serine (S) or proline (P) residues. In particular such embodiments, each of said residues (Xaa) is identical, i.e. said random coil domain consists of four different amino acid resdues. In particular such embodiments, each (Xaa) is a valine (V). In particular such embodiments, said random coil domain is selected from $(VPASA)_{20}$ (SEQ ID NO: 12) and $(VAPSA)_{20}$ (SEQ ID NO: 13).

Figure 4:
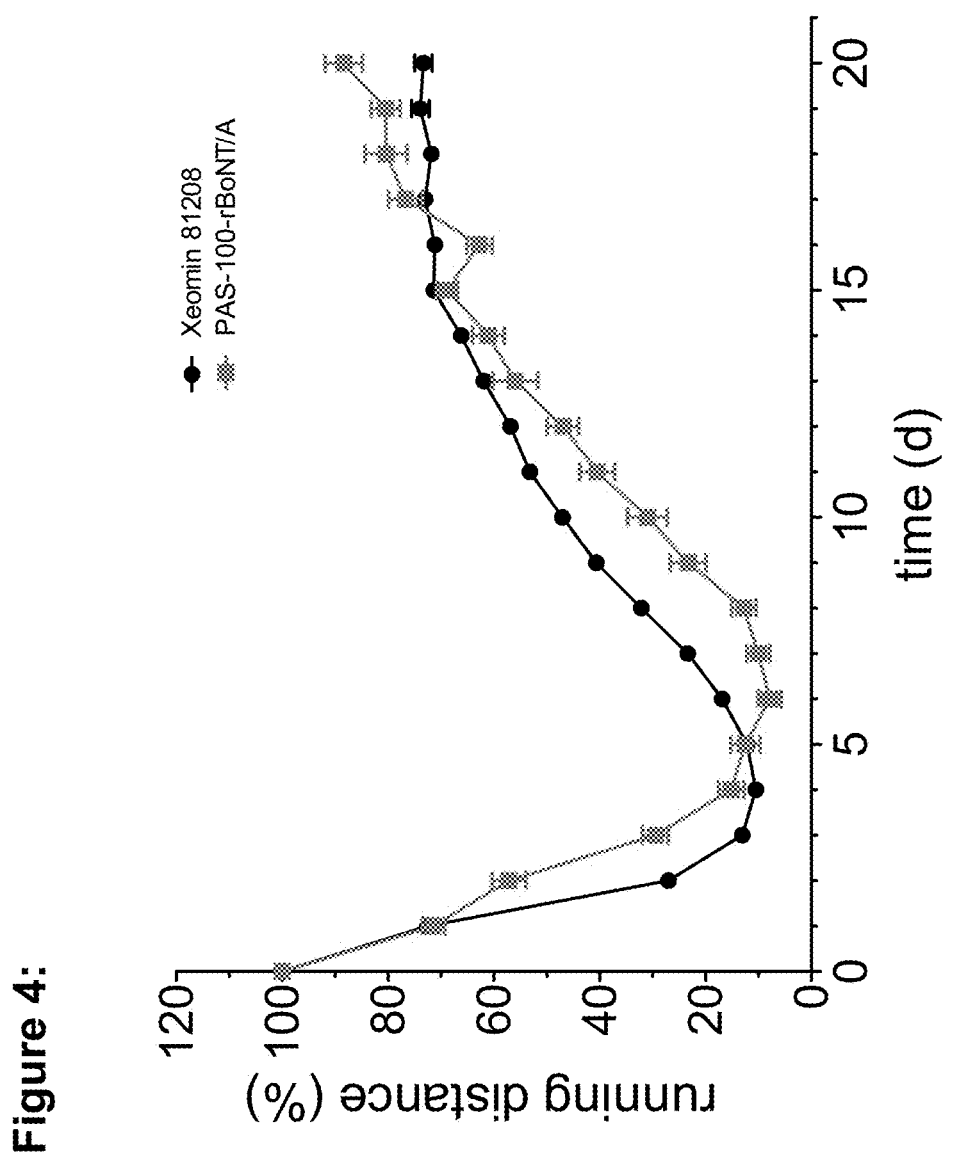
Figure 5:
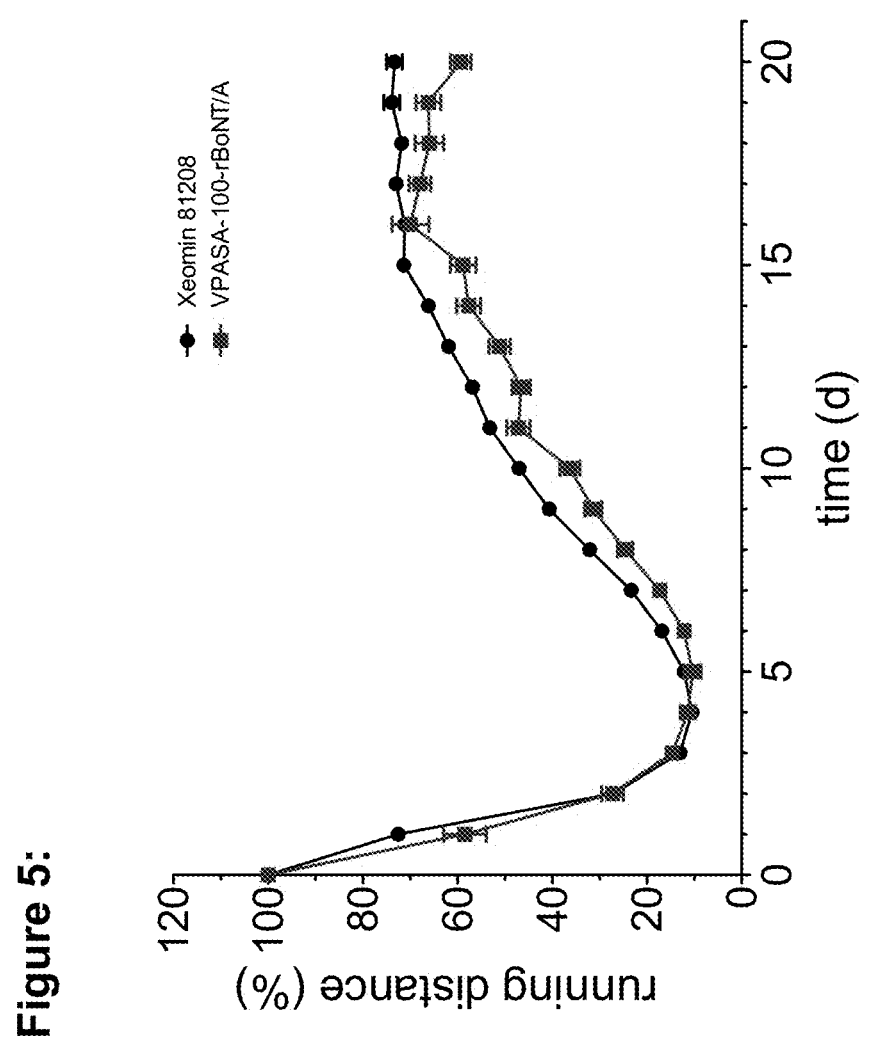

Surprising, protein segments of the type $(VPASA)_{20}$ and $(VAPSA)_{20}$ result in botulinum neurotoxin fusion domains, which do not only show an increased duration of biological persistence (as seen for pasylated sequences consisting of P, A, and S only, but also exhibit a rapid onset of biological activity similar to wild-type botulinum neurotoxins (see FIG. 5). This is in contrast to the performance of pasylated sequences consisting of P, A, and S only, which exhibit a delayed onset of biological activity (see FIGS. 4 and 5).

In particular embodiments, said random coil domain is inserted at (i) the N-terminus of the light chain of said recombinant clostridial neurotoxin; (ii) the C-terminus of the light chain of said recombinant clostridial neurotoxin; (iii) the N-terminus of the heavy chain of said recombinant clostridial neurotoxin; or (iv) the C-terminus of the heavy chain of said recombinant clostridial neurotoxin, particularly at the N-terminus of the light chain of said recombinant clostridial neurotoxin.

In particular embodiments, the sequence of said clostridial neurotoxin is selected from the sequence of (i) a *Clostridium botulinum* neurotoxin serotype A, B, C, D, E, F, and G, particularly *Clostridium botulinum* neurotoxin serotype A, C and E, particularly *Clostridium botulinum* neurotoxin serotype A, or (ii) from the sequence of a functional variant of a *Clostridium botulinum* neurotoxin of (i), or (iii) from the sequence of a chimeric *Clostridium botulinum* neurotoxin, wherein the clostridial neurotoxin light chain and heavy chain are from different parental clostridial neurotoxin serotypes.

In the context of the present invention, the term "*Clostridium botulinum* neurotoxin serotype A, B, C, D, E, F, and G" refers to neurotoxins found in and obtainable from *Clostridium botulinum*. Currently, seven serologically distinct types, designated serotypes A, B, C, D, E, F, and G are known, including certain subtypes (e.g. A1, A2, A3, A4 and A5).

In particular embodiments the clostridial neurotoxin is selected from a *Clostridium botulinum* neurotoxin serotype A, C and E, in particular from *Clostridium botulinum* neurotoxin serotype A, or from a functional variant of any such *Clostridium botulinum* neurotoxin.

In particular embodiments, said recombinant clostridial neurotoxin has a light chain and a heavy chain comprised in the amino acid sequence as found in SEQ ID NO: 8, SEQ ID NO: 10, SEQ ID NO: 14, or SEQ ID NO: 15.

In the context of the present invention, the term "functional variant of a clostridial neurotoxin" refers to a neurotoxin that differs in the amino acid sequence and/or the nucleic acid sequence encoding the amino acid sequence from a clostridial neurotoxin, but is still functionally active. In the context of the present invention, the term "functionally active" refers to the property of a recombinant clostridial neurotoxin to exhibit a biological activity of at least about 50%, particularly to at least about 60%, at least about 70%, at least about 80%, and most particularly at least about 90% of the biological activity of a naturally occurring parental clostridial neurotoxin, i.e. a parental clostridial neurotoxin without random coil domain, where the biological functions include, but are not limited to, binding to the neurotoxin receptor, entry of the neurotoxin into a neuronal cell, release of the light chain from the two-chain neurotoxin, and endopeptidase activity of the light chain, and thus inhibition of neurotransmitter release from the affected nerve cell.

On the protein level, a functional variant will maintain key features of the corresponding clostridial neurotoxin, such as key residues for the endopeptidase activity in the light chain, or key residues for the attachment to the neurotoxin receptors or for translocation through the endosomal membrane in the heavy chain, but may contain one or more mutations comprising a deletion of one or more amino acids of the corresponding clostridial neurotoxin, an addition of one or more amino acids of the corresponding clostridial neurotoxin, and/or a substitution of one or more amino acids of the corresponding clostridial neurotoxin. Particularly, said deleted, added and/or substituted amino acids are consecutive amino acids. According to the teaching of the present invention, any number of amino acids may be added, deleted, and/or substituted, as long as the functional variant remains biologically active. For example, 1, 2, 3, 4, 5, up to 10, up to 15, up to 25, up to 50, up to 100, up to 200, up to 400, up to 500 amino acids or even more amino acids may be added, deleted, and/or substituted. Accordingly, a functional variant of the neurotoxin may be a biologically active fragment of a naturally occurring neurotoxin. This neurotoxin fragment may contain an N-terminal, C-terminal, and/or one or more internal deletion(s).

In another embodiment, the functional variant of a clostridial neurotoxin additionally comprises a signal peptide. Usually, said signal peptide will be located at the N-terminus of the neurotoxin. Many such signal peptides are known in the art and are comprised by the present invention. In particular, the signal peptide results in transport of the neurotoxin across a biological membrane, such as the membrane of the endoplasmic reticulum, the Golgi membrane or the plasma membrane of a eukaryotic or prokaryotic cell. It has been found that signal peptides, when attached to the neurotoxin, will mediate secretion of the neurotoxin into the supernatant of the cells. In certain embodiments, the signal peptide will be cleaved off in the course of, or subsequent to, secretion, so that the secreted protein lacks the N-terminal signal peptide, is composed of separate light and heavy chains, which are covalently linked by disulfide bridges, and is proteolytically active.

In particular embodiments, the functional variant has in its *clostridium* neurotoxin part a sequence identity of at least about 40%, at least about 50%, at least about 60%, at least about 70% or most particularly at least about 80%, and a sequence homology of at least about 60%, at least about 70%, at least about 80%, at least about 90%, or most particularly at least about 95% to the corresponding part in the parental clostridial neurotoxin. Methods and algorithms for determining sequence identity and/or homology, including the comparison of variants having deletions, additions, and/or substitutions relative to a parental sequence, are well known to the practitioner of ordinary skill in the art. On the DNA level, the nucleic acid sequences encoding the functional homologue and the parental clostridial neurotoxin may differ to a larger extent due to the degeneracy of the genetic code. It is known that the usage of codons is different between prokaryotic and eukaryotic organisms. Thus, when expressing a prokaryotic protein such as a clostridial neurotoxin, in a eukaryotic expression system, it may be necessary, or at least helpful, to adapt the nucleic acid sequence to the codon usage of the expression host cell, meaning that sequence identity or homology may be rather low on the nucleic acid level.

In the context of the present invention, the term "variant" refers to a neurotoxin that is a chemically, enzymatically, or genetically modified derivative of a corresponding clostridial neurotoxin, including chemically or genetically modified neurotoxin from *C. botulinum*, particularly of *C. botulinum* neurotoxin serotype A, C or E. A chemically modified derivative may be one that is modified by pyruvation, phosphorylation, sulfatation, lipidation, pegylation, glycosylation and/or the chemical addition of an amino acid or a polypeptide comprising between 2 and about 100 amino acids, including modification occurring in the eukaryotic host cell used for expressing the derivative. An enzymatically modified derivative is one that is modified by the activity of enzymes, such as endo- or exoproteolytic enzymes, including modification by enzymes of the eukaryotic host cell used for expressing the derivative. As pointed out above, a genetically modified derivative is one that has been modified by deletion or substitution of one or more amino acids contained in, or by addition of one or more amino acids (including polypeptides comprising between 2 and about 100 amino acids) to, the amino acid sequence of said clostridial neurotoxin. Methods for designing and constructing such chemically or genetically modified derivatives and for testing of such variants for functionality are well known to anyone of ordinary skill in the art.

In particular embodiments, said recombinant clostridial neurotoxin shows increased duration of effect relative to an identical clostridial neurotoxin without the random coil domain.

In the context of the present invention, the term "increased duration of effect" or "increased duration of action" refers to a longer lasting denervation mediated by a clostridial neurotoxin of the present invention. For example, as disclosed herein, administration of a disulfide-linked di-chain clostridial neurotoxin comprising a random coil domain results in localized paralysis for a longer period of time relative to administration of an identical disulfide-linked di-chain clostridial neurotoxin without the coiled coil domain.

In the context of the present invention, the term "increased duration of effect/action" is defined as a more than about 20%, particularly more than about 50%, more particularly more than about 90% increased duration of effect of the recombinant neurotoxin of the present invention relative to the identical neurotoxin without the random coil domain.

In the context of the present invention the term "denervation" refers to denervation resulting from administration of a chemodenervating agent, for example a neurotoxin.

In the context of the present invention, the term "localized denervation" or "localized paralysis" refers to denervation of a particular anatomical region, usually a muscle or a group of anatomically and/or physiologically related muscles, which results from administration of a chemodenervating agent, for example a neurotoxin, to the particular anatomical region.

Without wishing to be bound by theory, the recombinant clostridial neurotoxins of the present invention might show increased biological half-life, reduced degradation rates, decreased diffusion rates, increased uptake by neuronal cells, and/or modified intracellular translocation rates, in each case relative to an identical parental clostridial neurotoxin without the random coil domain.

In particular embodiments, the increased duration of effect is due to an increased biological half-life.

In the context of the present invention, the term "biological half-life" specifies the lifespan of a protein, for example of a clostridial neurotoxin, in vivo. In the context of the present invention, the term "biological half-life" refers to the period of time, by which half of a protein pool is degraded in vivo. For example it refers to the period of time, by which half of the amount of clostridial neurotoxin of one administered dosage is degraded.

In the context of the present invention, the term "increased biological half-life" is defined as a more than about 20%, particularly more than about 50%, more particularly more than about 90% increased biological half-life of the recombinant neurotoxin of the present invention relative to the identical neurotoxin without the random coil domain.

In the context of the present invention, the term "reduced degradation rate" means that the random coil domain (PAS sequence) protects the light chain against degradation processes in the cytosol of the neuron such as, for example, the attack of proteases or modifying enzymes like E3 ligases. Because of this protection the half-life of the light chain in the neuron is extended resulting in a longer duration of the therapeutic effect.

In particular embodiments, the recombinant clostridial neurotoxin is for the use in the treatment of a disease requiring improved chemodenervation, wherein the recombinant clostridial neurotoxin causes longer lasting denervation relative to an identical clostridial neurotoxin without the random coil domain.

In particular other embodiments, the recombinant clostridial neurotoxin is for use in the treatment of (a) patients showing an immune reaction against BoNT/A, or (b) headache or epilepsy, wherein the recombinant clostridial neurotoxin is of serotype E.

In another aspect, the present invention relates to a pharmaceutical composition comprising the recombinant clostridial neurotoxin of the present invention.

In particular embodiments, the recombinant clostridial neurotoxin of the present invention or the pharmaceutical composition of the present invention is for use in the treatment of a disease or condition taken from the list of: cervical dystonia (spasmodic torticollis), blepharospasm, severe primary axillary hyperhidrosis, achalasia, lower back pain, benign prostate hypertrophy, chronic focal painful neuropathies, migraine and other headache disorders.

Additional indications where treatment with botulinum neurotoxins is currently under investigation and where the pharmaceutical composition of the present invention may be used, include pediatric incontinence, incontinence due to overactive bladder, and incontinence due to neurogenic bladder, anal fissure, spastic disorders associated with injury or disease of the central nervous system including trauma, stroke, multiple sclerosis, Parkinson's disease, or cerebral palsy, focal dystonias affecting the limbs, face, jaw or vocal cords, temporomandibular joint (TMJ) pain disorders, diabetic neuropathy, wound healing, excessive salivation, vocal cord dysfunction, reduction of the Masseter muscle for decreasing the size of the lower jaw, treatment and prevention of chronic headache and chronic musculoskeletal pain, treatment of snoring noise, assistance in weight loss by increasing the gastric emptying time.

Most recently, clostridial neurotoxins have been evaluated for the treatment of other new indications, for example painful keloid, diabetic neuropathic pain, refractory knee pain, trigeminal neuralgia trigger-zone application to control pain, scarring after cleft-lip surgery, cancer and depression.

In yet another aspect, the present invention relates to the use of the composition of the present invention for cosmetic treatment.

In the context of the present invention, the term "cosmetic treatment" relates to uses in cosmetic or aesthetic applications, such as the treatment of wrinkles, crow's feet, frown lines etc.

In another aspect, the present invention relates to a method for the generation of the recombinant clostridial neurotoxin of the present invention, comprising the step of obtaining a recombinant nucleic acid sequence encoding a recombinant single-chain precursor clostridial neurotoxin by the insertion of a nucleic acid sequence encoding said random coil domain, in particular a random coil domain according to the present invention, into a nucleic acid sequence encoding a parental clostridial neurotoxin.

In the context of the present invention, the term "recombinant nucleic acid sequence" refers to a nucleic acid, which has been generated by joining genetic material from two different sources.

In the context of the present invention, the term "single-chain precursor clostridial neurotoxin" refers to a single-chain precursor for a disulfide-linked di-chain clostridial neurotoxin, comprising a functionally active clostridial neurotoxin light chain, a functionally active neurotoxin heavy chain, and a loop region linking the C-terminus of the light chain with the N-terminus of the heavy chain.

In the context of the present invention, the term "recombinant single-chain precursor clostridial neurotoxin" refers to a single-chain precursor clostridial neurotoxin comprising a heterologous random coil domain, i.e. a random coil domain from a species other than *Clostridium botulinum*.

In particular embodiments, the recombinant single-chain precursor clostridial neurotoxin comprises a protease cleavage site in said loop region.

Single-chain precursor clostridial neurotoxins have to be proteolytically cleaved to obtain the final biologically active clostridial neurotoxins. Proteolytic cleavage may either occur during heterologous expression by host cell enzymes, or by adding proteolytic enzymes to the raw protein material isolated after heterologous expression. Naturally occurring clostridial neurotoxins usually contain one or more cleavage signals for proteases which post-translationally cleave the single-chain precursor molecule, so that the final di- or multimeric complex can form. At present, clostridial neurotoxins are still predominantly produced by fermentation processes using appropriate *Clostridium* strains. During the fermentation process, the single-chain precursors are proteolytically cleaved by an unknown clostridial protease to obtain the biologically active di-chain clostridial neurotoxin. In cases, where the single-chain precursor molecule is the precursor of a protease, autocatalytic cleavage may occur. Alternatively, the protease can be a separate non-clostridial enzyme expressed in the same cell. WO 2006/076902 describes the proteolytic cleavage of a recombinant clostridial neurotoxin single-chain precursor at a heterologous recognition and cleavage site by incubation of the *E. coli* host cell lysate. The proteolytic cleavage is carried out by an unknown *E. coli* protease. In certain applications of recombinant expression, modified protease cleavage sites have been introduced recombinantly into the interchain region between the light and heavy chain of clostridial toxins, e.g. protease cleavage sites for human thrombin or other human proteases or non-human proteases (see WO 01/14570).

In particular embodiments, the protease cleavage site is a site that is cleaved by a protease selected from the list of: thrombin, trypsin, enterokinase, factor Xa, plant papain, insect papain, crustacean papain, enterokinase, human rhinovirus 3C protease, human enterovirus 3C protease, tobacco etch virus protease, Tobacco Vein Mottling Virus, subtilisin and caspase 3.

In a particular embodiment, the recombinant single-chain precursor clostridial neurotoxin further comprises a binding tag, particularly selected from the group comprising: glutathione-S-transferase (GST), maltose binding protein (MBP), a His-tag, a StrepTag, or a FLAG-tag.

In the context of the present invention, the term "parental clostridial neurotoxin" refers to an initial clostridial neurotoxin without a heterologous random coil domain, selected from a natural clostridial neurotoxin, a functional variant of a natural clostridial neurotoxin or a chimeric clostridial neurotoxin, wherein the clostridial neurotoxin light chain and heavy chain are from different clostridial neurotoxin serotypes.

In particular embodiments, the method for the generation of the recombinant clostridial neurotoxin of the present invention further comprises the step of heterologously expressing said recombinant nucleic acid sequence in a host cell, particularly in a bacterial host cell, more particularly in an *E. coli* host cell.

In certain embodiments, the *E. coli* cells are selected from *E. coli* XL1-Blue, Nova Blue, TOP10, XL10-Gold, BL21, and K12.

In particular embodiments, the method for the generation of the recombinant clostridial neurotoxin of the present invention additionally comprises at least one of the steps of (i) generating a disulfide-linked di-chain recombinant clostridial neurotoxin comprising a random coil domain by causing or allowing contacting of said recombinant single-chain precursor clostridial neurotoxin with an endoprotease and (ii) purification of said recombinant single-chain precursor clostridial neurotoxin or said disulfide-linked di-chain recombinant clostridial neurotoxin by chromatography.

In particular embodiments, the recombinant single-chain precursor clostridial neurotoxin, or the recombinant disulfide-linked di-chain clostridial neurotoxin, is purified after expression, or in the case of the recombinant disulfide-linked di-chain clostridial neurotoxin, after the cleavage reaction. In particular such embodiments, the protein is purified by chromatography, particularly by immunoaffinity chromatography, or by chromatography on an ion exchange matrix, a hydrophobic interaction matrix, or a multimodal chromatography matrix, particularly a strong ion exchange matrix, more particularly a strong cation exchange matrix.

In the context of the present invention, the term "causing . . . contacting of said recombinant single-chain precursor clostridial neurotoxin . . . with an endoprotease" refers to an active and/or direct step of bringing said neurotoxin and said endoprotease in contact, whereas the term "allowing contacting of a recombinant single-chain precursor clostridial neurotoxin . . . with an endoprotease" refers to an indirect step of establishing conditions in such a way that said neurotoxin and said endoprotease are getting in contact to each other.

In the context of the present invention, the term "endoprotease" refers to a protease that breaks peptide bonds of non-terminal amino acids (i.e. within the polypeptide chain). As they do not attack terminal amino acids, endoproteases cannot break down peptides into monomers.

In particular embodiments, cleavage of the recombinant single-chain precursor clostridial neurotoxin is near-complete.

In the context of the present invention, the term "near-complete" is defined as more than about 95% cleavage, particularly more than about 97.5%, more particularly more than about 99% as determined by SDS-PAGE and subsequent Western Blot or reversed phase chromatography.

In particular embodiments, cleavage of the recombinant single-chain precursor clostridial neurotoxin occurs at a heterologous cleavage signal located in the loop region of the recombinant precursor clostridial neurotoxin.

In particular embodiments, the cleavage reaction is performed with crude host cell lysates containing said single-chain precursor protein.

In other particular embodiments, the single-chain precursor protein is purified or partially purified, particularly by a first chromatographic enrichment step, prior to the cleavage reaction.

In the context of the present invention, the term "purified" relates to more than about 90% purity. In the context of the present invention, the term "partially purified" relates to purity of less than about 90% and an enrichment of more than about two fold.

In another aspect, the present invention relates to a recombinant single-chain clostridial neurotoxin, which is a precursor for the recombinant clostridial neurotoxin of the present invention Thus, in such aspect, the present invention relates to a recombinant single-chain precursor clostridial neurotoxin comprising a random coil domain, in particular a random coil domain according to the present invention.

In particular embodiments, said recombinant single-chain clostridial neurotoxin precursor for a disulfide-linked di-chain clostridial neurotoxin comprises a functionally active clostridial neurotoxin light chain, a functionally active neurotoxin heavy chain, a loop region linking the C-terminus of the light chain with the N-terminus of the heavy chain, and a random coil domain according to the present invention.

In particular embodiments, said random coil domain consists of the amino acid sequence $(Xaa)_x\text{-}[(P,A,S)_y\text{-}(Xaa)\text{-}]_z(P,A,S)_y\text{-}(Xaa)_x$, wherein Xaa is an amino acid residue independently selected from any naturally occurring amino acid residue, provided that at least one Xaa in $[(P,A,S)_y\text{-}(Xaa)\text{-}]_z$ is different from an alanine, serine or proline residue; particularly wherein Xaa is valine; (P,A,S) represents an amino acid residue independently selected from an alanine (A), a serine (S) and a proline (P) residue; x is a number independently selected from 0 and 1; y is a number independently selected from 3 and 4; and z is 9 or more, particularly z is a number between 9 and 750.

In particular such embodiments, y is 3, and z is 11 or more, particularly z is a number between 11 and 749, more particularly between 14 and 124, more particularly between 16 and 67, more particularly between 19 and 59, more particularly between 21 and 54, or more particularly 23, 24, or 25, or 35, 36, or 37, or 48, 49, or 50. In other particular such embodiments, y is 4, and z is 9 or more, particularly z is a number between 9 and 599, more particularly between 11 and 99, more particularly between 13 and 51, more particularly between 15 and 47, more particularly between 17 and 43, or more particularly 18, 19, or 20, or 28, 29, or 30, or 38, 39, or 40.

In particular embodiments, said random coil domain comprises an amino acid sequence consisting of at least 50 amino acid residues forming random coil conformation, particularly between 50 and 3000 amino acid residues, more particularly between 60 and 500 amino acid residues, more particularly between 70 and 260 amino acid residues, more particularly between 80 and 240 amino acid residues, more particularly between 90 and 220 amino acid residues, particularly 100 amino acid residues, 150 amino acid residues, or 200 amino acid residues.

In particular embodiments, said random coil domain consists of alanine, serine and proline residues.

In particular embodiments, said random coil domain comprises a plurality of amino acid repeats, wherein said repeat consist of Ala, Ser, and Pro residues and wherein no more than 6 consecutive amino acid residues are identical.

In particular embodiments, the proline residues comprised in said random coil domain constitute more than 4% and less than 40% of the amino acids of said random coil domain.

In particular embodiments, said random coil domain comprises at least one amino acid sequence selected from the group consisting of: $(VPASA)_{20}$ (SEQ ID NO: 12) and $(VAPSA)_{20}$ (SEQ ID NO: 13); or circular permuted versions or (a) multimer(s) of these sequences as a whole or parts of these sequences, particularly $(VPASA)_{20}$ (SEQ ID NO: 12).

In particular embodiments, said random coil domain is inserted at (i) the N-terminus of the light chain of said recombinant clostridial neurotoxin; (ii) the C-terminus of the light chain of said recombinant clostridial neurotoxin; (i) the N-terminus of the heavy chain of said recombinant clostridial neurotoxin; or (ii) the C-terminus of the heavy chain of said recombinant clostridial neurotoxin.

In particular embodiments, the sequence of said clostridial neurotoxin is selected from the sequence of (i) a *Clostridium botulinum* neurotoxin serotype A, B, C, D, E, F, and G, particularly *Clostridium botulinum* neurotoxin serotype A, C and E, more particularly *Clostridium botulinum* neurotoxin serotype A, or (ii) from the sequence of a functional variant of a *Clostridium botulinum* neurotoxin of (i), or (iii) from the sequence of a chimeric *Clostridium* botulinum neurotoxin, wherein the clostridial neurotoxin light chain and heavy chain are from different clostridial neurotoxin serotypes.

In particular embodiments, said recombinant single-chain clostridial neurotoxin has the amino acid sequence as found in SEQ ID NO: 14, or SEQ ID NO: 15 (see Table 1).

In another aspect, the present invention relates to a nucleic acid sequence encoding the recombinant single-chain clostridial neurotoxin of the present invention.

In another aspect, the present invention relates to a method for obtaining the nucleic acid sequence of the present invention, comprising the step of inserting a nucleic acid sequence encoding a random coil domain, in particular a random coil domain according to the present invention, into a nucleic acid sequence encoding a parental clostridial neurotoxin.

In another aspect, the present invention relates to a vector comprising the nucleic acid sequence of the present invention, or the nucleic acid sequence obtainable by the method of the present invention.

In another aspect, the present invention relates to a recombinant host cell comprising the nucleic acid sequence of the present invention, the nucleic acid sequence obtainable by the method of the present invention, or the vector of the present invention.

In certain embodiments, the recombinant host cells are selected from E. coli XL1-Blue, Nova Blue, TOP10, XL10-Gold, BL21, and K12.

In another aspect, the present invention relates to a method for producing the recombinant single-chain precursor clostridial neurotoxin of the present invention, comprising the step of expressing the nucleic acid sequence of the present invention, or the nucleic acid sequence obtainable by the method of the present invention, or the vector of the present invention in a recombinant host cell, or cultivating the recombinant host cell of the present invention under conditions that result in the expression of said nucleic acid sequence.

EXAMPLES

Comparative Example 1: Generation and Purification of a PASylated Botulinum Toxin Type A (PAS200-rBoNT/A)

The "PAS" module comprising 200 amino acid residues built from the amino acids proline, serine and alanine was synthetically produced and after digestion with SapI inserted at the N-terminus of recombinant BoNT/A (rBoNT/A) (FIG. 1). The correct cloning was verified by sequencing.

Figure 2:
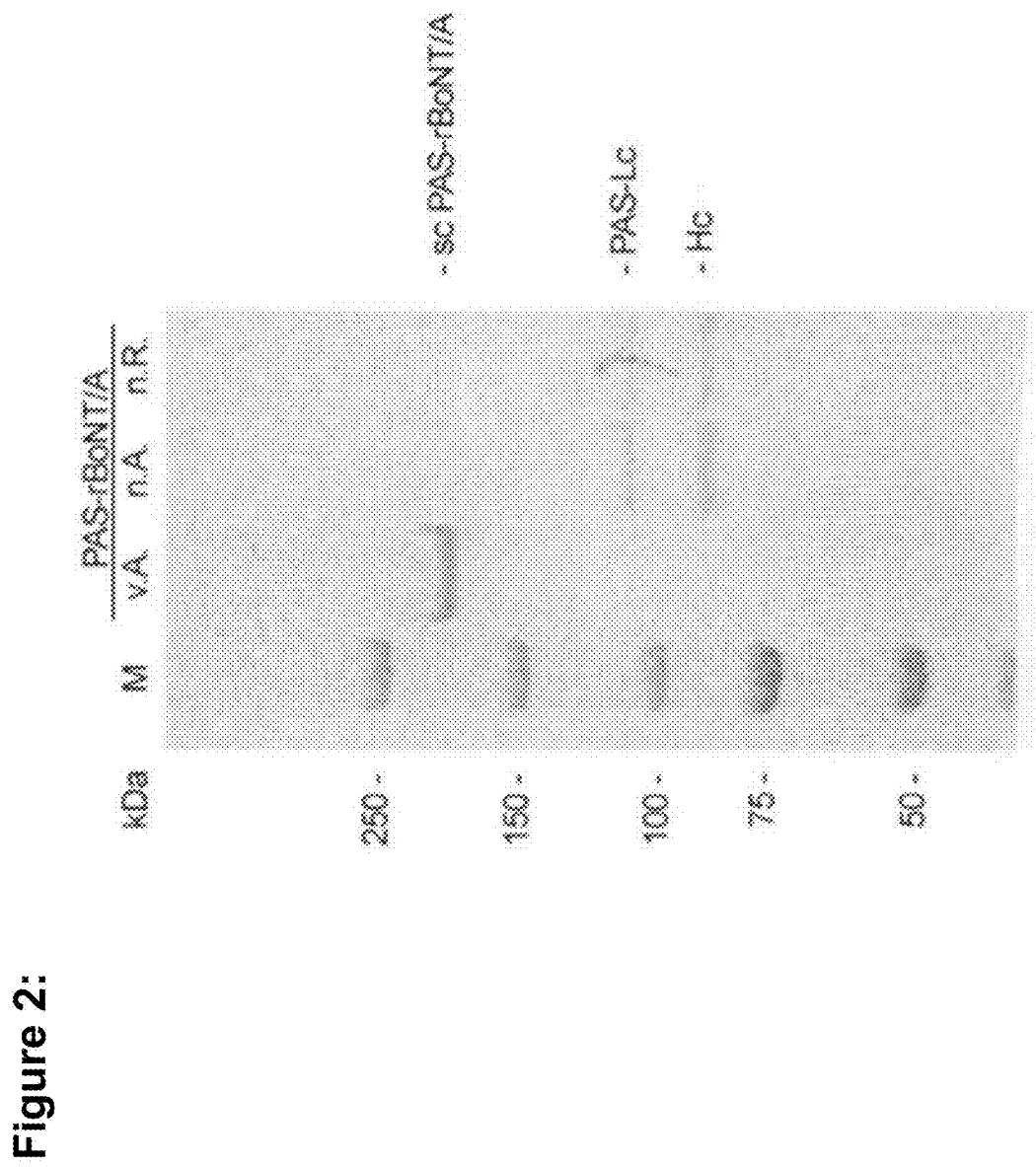
FIG. 2: SDS-PAGE of purified PAS-rBoNT/A. Prior to applying the samples to the gel, β-mercaptoethanol was added. Lane "v.A.": purified, non-activated single-chain PAS-rBoNT/A having a molecular weight (Mw) of about 175 kDa. Lanes "n.A." (after activation) and "n.R." (after purification) show light chain (PAS-Lc) and heavy chain (Hc) obtained after activation by thrombin under reducing conditions. The light chain runs with an apparent Mw of about 110 kDa well above the theoretical Mw of about 75 kDa.

Expression was performed in expression strain E. coli B121. Purification was done using a combination of affinity and size exclusion chromatography, followed by activation using thrombin. FIG. 2 summarizes the results of purification and activation.

Comparative Example 2: Measurement of Biological Activity in the Hemidiaphracima Test (HDA Test)

This ex vivo test performs all steps required for intoxication (target cell binding, internalisation and translocation into cytosol). In order to achieve that, a murine nerve-muscle preparation, comprising the hemidiaphragma and the Nervus phrenicus, is stimulated in an organ bath by a continuous frequency of 1 Hz. The resulting amplitude of muscle contraction is plotted against the time. After addition of the toxin sample to the organ bath, the time required for a 50% reduction of the amplitude seen without toxin is determined. This so-called paralytic half-time is a direct measure for the biological activity. In the case of PAS200-rBoNT/A, the paralytic half-time was 157 min at a concentration of 0.35 ng/ml in the organ bath. By comparison with a calibration curve established with wild-type BoNT/A, a specific biological activity of 60 pg/U can be calculated.

Figure 3:
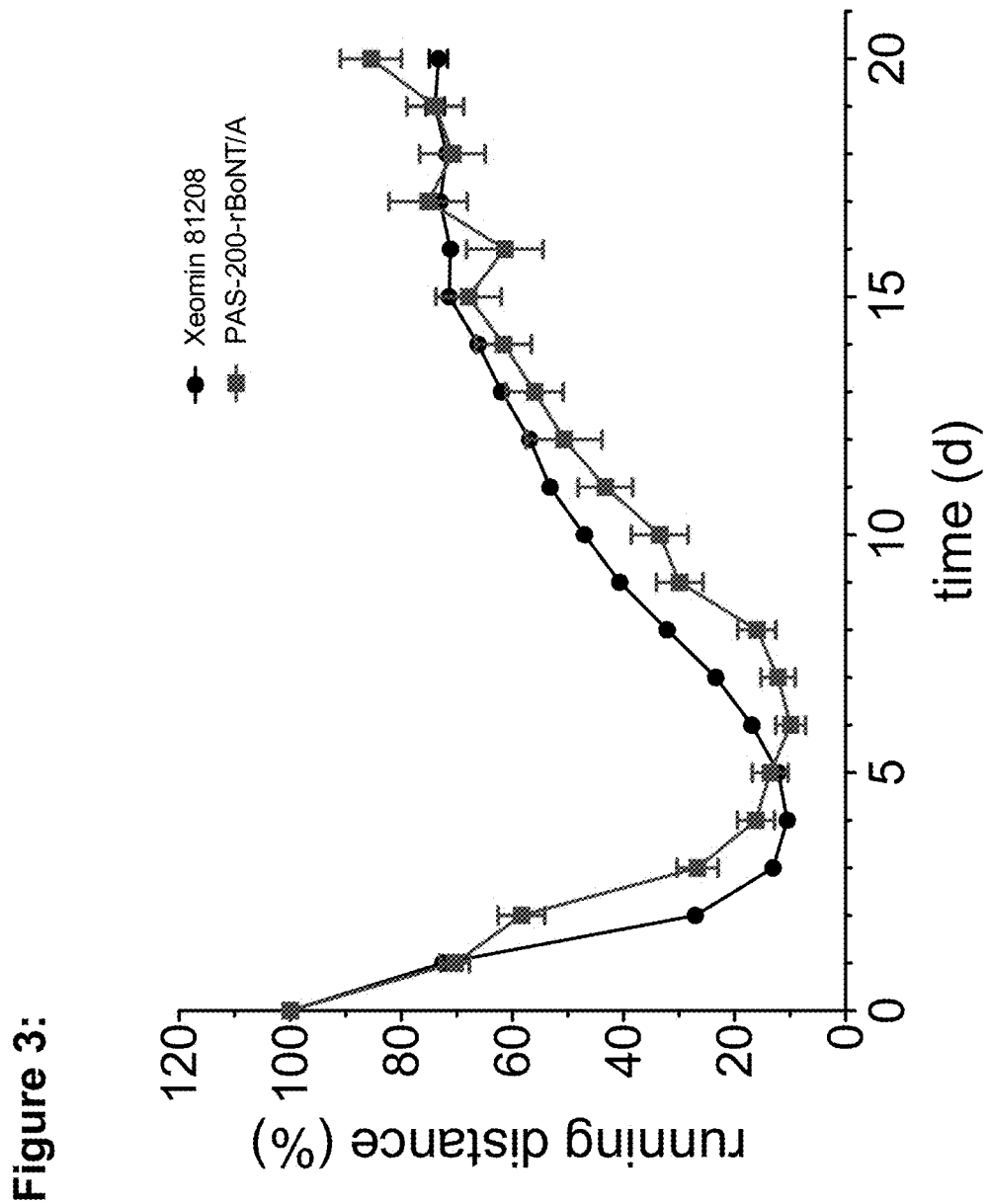
FIG. 3: Mouse running assay with PAS200-rBoNT/A: ■: PAS200-rBoNT/A, ●: mean of Standard (54 assays) from Xeomin 81208 (0,6U)

Comparative Example 3: Determination of Biological Activity in Vivo Using the "Digit Abduction Score" (DAS)-Test In this in vivo test, the biological activity of a sample is determined. Based on the results for the specific biological activity obtained in the HDA test (see Example 2) dosages are calculated that should result in a sub-maximum effect comparable to the effect seen with a standard sample run in parallel. Those dosages, in a volume of 20 μl in each case, are injected into the M. gastrocnemius of the right hindpaw of four mice in each case. The resulting effect is measured over time by determining the digit abduction when lifting the mouse and is quantified by using a score from 0 to 4 (Aoki, K. R.; Toxicon 39 (2001) 1815-1820). A score of 0 corresponds to maximum digit abduction, while a score of 4 corresponds to maximum paralysis, where digit abduction is completely absent. Scores 1, 2 or 3 describe intermediate states between these two extremes. In FIG. 3, the results of the DAS test with PAS200-rBoNT/A are shown.

Comparative Example 4: Duration of Effect of PAS200-rBoNT/A in a "Mouse Running Assay"

Based on the results for the activity obtained in the DAS test (see Example 3) dosages can be calculated that are suitable for a comparison of the duration of effect with a standard (Xeomin®) run in parallel. The aim is to apply an equipotent dose i.e. the maximum effect of sample and standard (Xeomin®) should be the same. Equipotent dosages of PAS200-rBoNT/A or Xeomin® were injected into the M. gastrocnemius of eight mice each that had been trained in a treadmill. Using these dosages, only a sub-maximum paralysis was observed in order to exclude potential systemic effects as far as possible, which may have an impact on the duration of effect. The daily running distance in the treadmill was measured over 15 days. The paralysis caused by the toxins was plotted as percentage of the running distance on the day before the injection, which was set as 100%, against the time (see FIG. 3).

The injection of PAS200-rBoNT/A resulted in a maximum paralysis after 4 days corresponding to that seen for the control group treated with Xeomin. During the recovery phase following the phase of maximum paralysis the running distance of the control group reached a value of 25% of the starting value after 8 days, whereas the group treated with PAS200-rBoNT/A reached that value only after 11 days. Thus, the duration of effective paralysis was significantly extended.

Comparative Example 5: Generation and Purification of a PASylated Botulinum Toxin Type A (PAS100-rBoNT/A)

PAS100-rBoNT/A comprising a "PAS" module comprising 100 amino acid residues built from the amino acids proline, serine and alanine was generated and purified as described for PAS200-rBoNT/A in Example 1.

Comparative Example 6: Duration of Effect of PAS100-rBoNT/A in a "Mouse Running Assay"

A mouse running assay using PAS100-rBoNT/A was performed as decribed in example 4. Equipotent dosages of PAS100-rBoNT/A or Xeomin® were injected into the *M. gastrocnemius* of eight mice each and the daily running distance in the treadmill was measured over 15 days. The paralysis caused by the toxins was plotted as percentage of the running distance on the day before the injection, which was set as 100%, against the time (see FIG. 4).

The injection of PAS100-rBoNT/A resulted in a maximum paralysis after 6 days, for the control group treated with Xeomin maximum paralysis was observed after 4 days. During the recovery phase the running distance of the control group reached a value of 40% of the starting value 4 days after maximum paralysis was observed (day 8), whereas the group treated with PAS100-rBoNT/A reached that value 5 days after maximum paralysis (day 11). Thus, the duration of effective paralysis was significantly extended.

Example 7: Generation and Purification of a VPASA100-Botulinum Toxin Type A (VPASA100-rBoNT/A)

VPASA100-rBoNT/A comprising a "VPASA" module comprising 100 amino acid residues built from the 20-fold repeat of amino acids valine, proline, serine and alanine, (VPASA)$_{20}$-rBoNT/A), was generated and purified as described for PAS200-rBoNT/A in Example 1.

Example 8: Generation and Purification of a VPASA100-Botulinum Toxin Type A (VAPSA100-rBoNT/A)

VAPSA100-rBoNT/A comprising a "VAPSA" module comprising 100 amino acid residues built from the 20-fold repeat of amino acids valine, proline, serine and alanine, (VAPSA)$_{20}$-rBoNT/A), was generated and purified as described for PAS200-rBoNT/A in Example 1.

Example 9: Duration of Effect of VPASA100-rBoNT/A in a "Mouse Running Assay"

A mouse running assay using VPASA100-rBoNT/A was performed as decribed in example 4. Equipotent dosages of VPASA100-rBoNT/A or Xeomin® were injected into the *M. gastrocnemius* of eight mice each and the daily running distance in the treadmill was measured over 15 days. The paralysis caused by the toxins was plotted as percentage of the running distance on the day before the injection, which was set as 100%, against the time (see FIG. 5).

During the recovery phase the running distance of the group treated with VPASA100-rBoNT/A reached the value of 40% markedly later than of the control group.

TABLE 1

Sequences

SEQ ID NO 1:
ASPAAPAPASPAAPAPSAPA

SEQ ID NO 2:
AAPASPAPAAPSAPAPAAPS

SEQ ID NO 3:
APSSPSPSAPSSPSPASPSS

SEQ ID NO 4:
SAPSSPSPSAPSSPSPASPS

SEQ ID NO 5:
SSPSAPSPSSPASPSPSSPA

SEQ ID NO 6:
AASPAAPSAPPAAASPAAPSAPPA

SEQ ID NO 7:
ASAAAPAAASAAASAPSAAA

SEQ ID NO 8: PAS200 rBoNT/A (amino acid sequence)
MGSSHHHHHHGSLVPRSSSASPAAPAPASPAAPAPSAPAASPAAPAPASPAAPAPSAPAA
SPAAPAPASPAAPAPSAPAASPAAPAPASPAAPAPSAPAASPAAPAPASPAAPAPSAPAA
SPAAPAPASPAAPAPSAPAASPAAPAPASPAAPAPSAPAASPAAPAPASPAAPAPSAPAA
SPAAPAPASPAAPAPSAPAASPAAPAPASPAAPAPSAPAAPFVNKQFNYKDPVNGVDIAY
IKIPNAGQMQPVKAFKIHNKIWVIPERDTFTNPEEGDLNPPPEAKQVPVSYYDSTYLSTD
NEKDNYLKGVTKLFERIYSTDLGRMLLTSIVRGIPFWGGSTIDTELKVIDINCINVIQPD
GSYRSEELNLVIIGPSADIIQFECKSFGHEVLNLTRNGYGSTQYIRFSPDFTFGFEESLE
VDTNPLLGAGKFATDPAVTLAHELIHAGHRLYGIAINPNRVFKVNTNAYYEMSGLEVSFE
ELRTFGGHDAKFIDSLQENEFRLYYYNKFKDIASTLNKAKSIVGTTASLQYMKNVFKEKY
LLSEDTSGKFSVDKLKFDKLYKMLTEIYTEDNFVKFFKVLNRKTYLNFDKAVFKINIVPK
VNYTIYDGFNLRNTNLAANFNGQNTEINNMNFTKLKNFTGLFEFYKLLCVRGIITSKAGA
GKSLVPRGSAGAGALNDLCIKVNNWDLFFSPSEDNFTNDLNKGEEITSDTNIEAAEENIS
LDLIQQYYLTFNFDNEPENISIENLSSDIIGQLELMPNIERFPNGKKYELDKYTMFHYLR
AQEFEHGKSRIALTNSVNEALLNPSRVYTFFSSDYVKKVNKATEAAMFLGWVEQLVYDFT
DETSEVSTTDKIADITIIIPYIGPALNIGNMLYKDDFVGALIFSGAVILLEFIPEIAIPV
LGTFALVSYIANKVLTVQTIDNALSKRNEKWDEVYKYIVTNWLAKVNTQIDLIRKKMKEA
LENQAEATKAIINYQYNQYTEEEKNNINFNIDDLSSKLNESINKAMININKFLNQCSVSY
LMNSMIPYGVKRLEDFDASLKDALLKYIYDNRGTLIGQVDRLKDKVNNTLSTDIPFQLSK TABLE 1-continued Sequences YVDNQRLLSTFTEYIKNIINTSILNLRYESNHLIDLSRYASKINIGSKVNFDPIDKNQIQ
LFNLESSKIEVILKNAIVYNSMYENFSTSFWIRIPKYFNSISLNNEYTIINCMENNSGWK
VSLNYGEIIWTLQDTQEIKQRVVFKYSQMINISDYINRWIFVTITNNRLNNSKIYINGRL
IDQKPISNLGNIHASNNIMFKLDGCRDTHRYIWIKYFNLFDKELNEKEIKDLYDNQSNSG
ILKDFWGDYLQYDKPYYMLNLYDPNKYVDVNNVGIRGYMYLKGPRGSVMTTNIYLNSSLY
RGTKFIIKKYASGNKDNIVRNNDRVYINVVVKNKEYRLATNASQAGVEKILSALEIPDVG
NLSQVVVMKSKNDQGITNKCKMNLQDNNGNDIGFIGFHQFNNIAKLVASNWYNRQIERSS
RTLGCSWEFIPVDDGWGERPLGDLVPRGSANSSSVDKLWSHPQFEK SEQ ID NO 9: PAS100 rBoNT/A (amino acid sequence)
MGSSHHHHHHGSLVPRSSSASPAAPAPASPAAPAPSPAAPSPAAPAPASPAAPAPSAPAA
SPAAPAPASPAAPAPSAPAASPAAPAPASPAAPAPSAPAASPAAPAPASPAAPAPSAPAA
PFVNKQFNYKDPVNGVDIAYIKIPNAGQMQPVKAFKIHNKIWVIPERDTFTNPEEGDLNP
PPEAKQVPVSYYDSTYLSTDNEKDNYLKGVTKLFERIYSTDLGRMLLTSIVRGIPFWGGS
TIDTELKVIDTNCINVIQPDGSYRSEELNLVIIGPSADIIQFECKSFGHEVLNLTRNGYG
STQYIRFSPDFTFGFEESLEVDTNPLLGAGKFATDPAVTLAHELIHAGHRLYGIAINPNR
VFKVNTNAYYEMSGLEVSFEELRTFGGHDAKFIDSLQENEFRLYYYNKFKDIASTLNKAK
SIVGTTASLQYMKNVFKEKYLLSEDTSGKFSVDKLKFDKLYKMLTEIYTEDNFVKFFKVL
NRKTYLNFDKAVFKINIVPKVNYTIYDGFNLRNTNLAANFNGQNTEINNMNFTKLKNFTG
LFEFYKLLCVRGIITSKAGAGKSLVPRGSAGAGALNDLCIKVNNWDLFFSPSEDNFTNDL
NKGEEITSDTNIEAAEENISLDLIQQYYLTFNFDNEPENISIENLSSDIIGQLELMPNIE
RFPNGKKYELDKYTMFHYLRAQEFEHGKSRIALTNSVNEALLNPSRVYTFFSSDYVKKVN
KATEAAMFLGWVEQLVYDFTDETSEVSTTDKIADITIIIPYIGPALNIGNMLYKDDFVGA
LIFSGAVILLEFIPEIAIPVLGTFALVSYIANKVLTVQTIDNALSKRNEKWDEVYKYIVT
NWLAKVNTQIDLIRKKMKEALENQAEATKAIINYQYNQYTEEEKNNINFNIDDLSSKLNE
SINKAMININKFLNQCSVSYLMNSMIPYGVKRLEDFDASLKDALLKYIYDNRGTLIGQVD
RLKDKVNNTLSTDIPFQLSKYVDNQRLLSTFTEYIKNIINTSILNLRYESNHLIDLSRYA
SKINIGSKVNFDPIDKNQIQLFNLESSKIEVILKNAIVYNSMYENFSTSFWIRIPKYFNS
ISLNNEYTIINCMENNSGWKVSLNYGEIIWTLQDTQEIKQRVVFKYSQMINISDYINRWI
FVTITNNRLNNSKIYINGRLIDQKPISNLGNIHASNNIMFKLDGCRDTHRYIWIKYFNLF
DKELNEKEIKDLYDNQSNSGILKDFWGDYLQYDKPYYMLNLYDPNKYVDVNNVGIRGYMY
LKGPRGSVMTTNIYLNSSLYRGTKFIIKKYASGNKDNIVRNNDRVYINVVVKNKEYRLAT
NASQAGVEKILSALEIPDVGNLSQVVVMKSKNDQGITNKCKMNLQDNNGNDIGFIGFHQF
NNIAKLVASNWYNRQIERSSRTLGCSWEFIPVDDGWGERPLGDLVPRGSANSSSVDKLWS
HPQFEK SEQ ID NO 10: PAS200 rBoNT/A (nucleic acid sequence)
ATGGGCAGCAGCCATCATCATCACCATCATGGTAGCCTGGTTCCGCGTAGCTCTTCTGCA
AGTCCGGCAGCACCGGCACCGGCTTCACCAGCTGCACCAGCACCTAGCGCACCGGCAGCA
TCTCCAGCAGCCCCTGCACCGGCAAGCCCTGCAGCTCCAGCACCGTCAGCACCAGCAGCA
AGCCCAGCTGCTCCTGCTCCAGCGAGCCCAGCAGCGCCAGCTCCTAGTGCCCCTGCTGCC
TCTCCTGCTGCTCCGGCACCAGCAAGTCCTGCTGCGCCTGCACCGAGTGCTCCGGCTGCT
AGTCCTGCCGCACCAGCTCCGGCTAGTCCAGCTGCTCCAGCCCCTTCAGCTCCGGCAGCT
TCCCCTGCAGCGCCTGCCCCTGCCAGTCCAGCGGCTCCTGCACCTAGTGCGCCTGCAGCT
TCACCGGCTGCCCCTGCGCCAGCTTCTCCTGCGGCTCCAGCTCCATCTGCCCCAGCCGCA
TCCCCAGCGGCACCAGCTCCAGCTTCTCCGGCAGCGCCAGCACCTTCTGCGCCTGCCGCA
TCTCCTGCAGCACCAGCGCCTGCGAGTCCTGCAGCTCCTGCTCCTTCAGCCCCTGCGGCA
AGTCCAGCAGCACCAGCCCCAGCAAGCCCAGCCGCACCAGCACCATCTGCCCCTGCAGCA
CCATTTGTGAACAAGCAGTTTAACTATAAGGACCCGGTGAACGGTGTGGATATCGCGTAT
ATCAAAATCCCGAATGCGGGCCAGATGCAACCAGTCAAGGCGTTCAAGATTCATAACAAG
ATTTGGGTTATTCCGGAACGTGATACCTTCACCAATCCGGAAGAAGGCGACTTAAACCCG
CCGCCAGAAGCCAAACAAGTGCCGGTGAGCTACTATGATAGCACGTATCTTAGCACCGAT
AATGAAAAAGACAATTACCTGAAGGGCGTGACCAAGTTGTTCGAGCGCATCTACAGTACC
GACTTAGGCCGCATGTTGTTGACGAGCATCGTTCGCGGTATCCCGTTCTGGGGCGGCTCG
ACCATTGATACCGAGTTGAAAGTCATTGACACGAACTGTATCAATGTTATCCAACCGGAC
GGCAGTTATCGCAGCGAGGAGTTAAATTTGGTCATCATCGGTCCAAGCGCAGATATTATT
CAGTTCGAATGCAAGAGCTTCGGCCATGAGGTCTTGAATTTGACGCGCAACGGTTACGGC
AGCACCCAATACATCCGCTTTAGCCCGGATTTCACCTTTGGCTTCGAGGAGAGCTTGGAG
GTGGACACCAACCCGCTGTTAGGTGCCGGCAAATTCGCAACCGACCCGGCAGTGACGTTG
GCGCACGAATTGATTCATGCGGGTCACCGCTTATACGGTATCGCGATCAATCCGAATCGC
GTCTTTAAAGTCAATACCAACGCGTACTACGAAATGAGCGGCTTAGAAGGTTAGCTTTGAA
GAATTACGCACCTTCGGTGGCCACGACGCCAAGTTCATCGACAGCCTGCAGGAAATGAG
TTCCGCTTGTACTATTACAATAAATTCAAGGACATCGCGAGCACCTTAAATAAAGCAAAG
AGCATTGTGGGCACCACCGCAAGCTTGCAGTACATGAAGAACGTATTTAAGGAAAAATAT
TTGTTGTCGGAGGATACCAGCGGGAAATTCAGCGTCGATAAGCTGAAATTCGACAAATTG
TATAAAATGCTGACCGAGATTTACACCGAGGATAACTTCGTCAAGTTTTTTAAGGTGTTA
AATCGTAAGACCTATTTAAACTTTGATAAAGCGGTGTTTAAAATTAATATCGTGCCGAAG
GTGAATTACACCATCTACGATGGTTTCAATTTACGCAACACGAATCTGGCGGCGAATTTT
AATGGCCAAAACACCGAAATTAACAACATGAACTTTACGAAGTTAAAGAATTTCACGGGC
TTATTCGAATTCTACAAGTTATTATGCGTGCGCGGCATCATTACCAGCAAGGCAGGTGCG
GGCAAGTCCTTGGTTCCGCGTGGCAGCGCCGGCGCCGGCGCGCTCAATGATCTGTGTATT
AAAGTCAATAACTGGGACCTGTTCTTCAGCCCGAGCGAGGATAACTTTACCAACGACTTA
AACAAAGGCGAGGAGATCACGAGCGATACGAACATCGAGGCGGCGGAGAAAATATTAGC
CTGGACCTCATTCAGCAGTACTATCTGACGTTCAATTTTGACAATGAGCCGGAGAACATC
AGCATTGAAAATCTCAGCAGCGACATCATCGGTCAGTTGGAACTGATGCCGAACATTGAA
CGCTTTCCGAACGGCAAAAAATATGAACTGGACAAGTATACCATGTTCCATTACTTACGC
GCACAGGAATTTGAGCACGGCAAGAGCCGCATTGCGCTGACCAATAGCGTTAACGAGGCC
TTGTTAAATCCGAGCCGTGTCTACACGTTCTTCAGCAGCGATTATGTCAAAAAAGTGAAC TABLE 1-continued Sequences AAGGCGACCGAAGCCGCGATGTTTTTGGGCTGGGTCGAGCAATTGGTTTACGATTTTACC
GACGAAACCAGCGAGGTGAGCACGACCGACAAAATTGCAGATATCACCATCATCATTCCG
TACATCGGTCCGGCGCTCAATATCGGCAATATGTTATACAAGGACGACTTTGTGGGCGCG
CTGATCTTTAGCGGCGCGGTTATCTTATTAGAATTCATCCCGGAGATCGCAATCCCGGTC
TTGGGCACCTTTGCGTTGGTGAGCTATATCGCGAATAAAGTGCTCACGGTCCAAACCATC
GATAACGCGCTCAGCAAGCGTAATGAGAAATGGGACGAGGTTTATAAGTATATCGTGACC
AACTGGTTAGCAAAAGTCAATACGCAGATCGATCTCATCCGCAAAAAAATGAAAGAAGCC
TTGGAAAATCAAGCGGAGGCAACCAAAGCCATCATTAATTACCAGTATAACCAATATACC
GAAGAAGAAAAAAACAATATCAACTTCAATATCGATGATTTGAGCAGCAAACTGAACGAG
AGCATTAACAAAGCGATGATTAACATCAACAAGTTCTTGAATCAATGCAGCGTGAGCTAT
CTCATGAACAGCATGATCCCGTATGGCGTCAAACGCTTGGAAGATTTTGACGCCAGCCTG
AAAGATGCGCTCCTCAAGTATATTTATGACAACCGCGGCACCCTCATTGGCCAGGTGGAC
CGCTTGAAGGATAAAGTGAACAATACGCTCAGCACGGATATCCCGTTCCAGCTGAGCAAG
TACGTCGACAACCAGCGCTTACTGAGCACCTTTACCGAGTATATCAAGAACATCATTAAT
ACCAGCATCCTCAACTTGCGCTATGAGAGCAATCACCTGATCGACCTCAGCCGCTACGCC
AGCAAGATCAACATCGGCAGCAAGGTCAATTTCGACCCGATCGATAAGAATCAGATCCAA
TTGTTTAACCTGGAAAGCAGCAAGATCGAGGTTATCTTGAAGAACGCGATTGTGTACAAC
AGCATGTACGAGAACTTTAGCACGAGCTTCTGGATTCGTATCCCGAAGTATTTCAATAGC
ATTAGCCTGAATAACGAATATACCATTATCAACTGCATGGAAAATAATAGCGGCTGGAAG
GTGAGCTTAAATTACGGCGAGATCATTTGGACCTTACAGGATACCCAAGAAATCAAACAG
CGCGTCGTCTTTAAGTATAGCCAGATGATCAACATCAGCGATTACATCAACCGCTGGATC
TTCGTGACCATCACCAATAATCGCTTGAATAATAGCAAGATTTACATCAATGGTCGCTTG
ATTGATCAAAAACCGATCAGCAATCTCGGTAATATCCATGCCAGCAATAACATCATGTTT
AAGTTAGACGGTTGCCGCGATACCCACCGCTATATCTGGATCAAGTATTTTAACTTATTT
GATAAGGAACTCAACGAAAAGGAAATTAAAGACTTATATGACAATCAGAGCAATAGCGGC
ATCCTGAAGGATTTCTGGGGCGACTACCTGCAGTACGATAAGCCGTACTATATGTTGAAC
TTGTATGACCCGAACAAATATGTCGATGTGAACAATGTGGGTATTCGTGGCTATATGTAC
TTAAAGGGCCCGCGTGGTAGCGTGATGACCACGAATATTTACTTAAACAGCAGCTTATAC
CGCGGCACGAAGTTTATTATCAAGAAGTATGCCAGCGGCAACAAGGACAATATCGTCCGC
AACAACGACCGTGTGTATATTAACGTGGTGGTGAAGAATAAAGAGTACCGCTTGGCCACG
AATGCGAGCCAGGCGGGCGTGGAAAAAATCTTGAGCGCGTTGGAGATCCCGGACGTCGGC
AACCTCAGCCAGGTTGTGGTGATGAAGTCTAAAAACGACCAGGGCATCACGAACAAGTGC
AAAATGAATTTGCAAGATAACAACGGCAACGACATCGGCTTTATTGGTTTTCACCAGTTC
AATAACATCGCCAAACTCGTGGCCAGCAATTGGTATAACCGCCAAATTGAACGCAGCAGC
CGCACGCTCGGCTGTAGCTGGGAGTTCATCCCGGTGGACGATGGCTGGGGCGAGCGCCCG
CTCGGAGATCTGGTGCCACGCGGTTCCGCGAATTCGAGCTCCGTCGACAAGCTTGGAGC
CACCCGCAGTTCGAAAAATAA SEQ ID NO 11: PAS100 rBoNT/A (nucleic acid sequence)
ATGGGTAGCAGCCATCATCATCATCATCATGGTAGCCTGGTTCCGCGTAGCTCTTCTGCA
AGTCCGGCAGCACCGGCACCGGCTTCACCAGCTGCACCAGCACCTAGCGCACCGGCAGCA
TCTCCAGCAGCCCCTGCACCGGCAAGCCCTGCAGCTCCAGCACCGTCAGCACCAGCAGCA
AGCCCAGCTGCTCCTGCTCCAGCGAGCCCAGCAGCGCCAGCTCCTAGTGCCCCTGCTGCC
TCTCCTGCTGCTCCGGCACCAGCAAGTCCTGCTGCGCCTGAGTGCTCCGGCTGCT
AGTCCTGCCGCACCAGCTCCGGCTAGTCCAGCTGCTCCAGCCCCTTCAGCCCCTGCAGCA
CCATTTGTGAACAAGCAGTTTAACTATAAGGACCCGGTGAACGGTGTGGATATCGCGTAT
ATCAAAATCCCGAATGCGGGCCAGATGCAACCAGTCAAGGCGTTCAAGATTCATAACAAG
ATTTGGGTTATTCCGGAACGTGATACCTTCACCAATCCGGAAGAAGGCGATTTAAATCCG
CCGCCAGAAGCCAAACAAGTGCCGGTGAGCTACTATGATAGCACGTATCTTAGCACCGAT
AATGAAAAAGACAATTACCTGAAGGGCGTGACCAAGTTGTTCGAGCGCATCTACAGTACC
GACTTAGGCCGCATGTTGTTGACGAGCATCGTCGCGGTATCCCGTTCTGGGGCGGCTCG
ACCATTGATACCGAGTTGAAAGTCATTGACACGAACTGTATCAATGTTATCCAACCGGAC
GGCAGTTATCGCAGCGAGGAGTTAAATTTGGTCATCATCGGTCCAAGCGCAGATATTATT
CAGTTCGAATGCAAGAGCTTCGGCCATGAGGTCTTGAATTTGACGCGCAACGGTTACGGC
AGCACCCAATACATCCGCTTTAGCCCGGATTTCACCTTTGGCTTCGAGGAGAGCTTGGAG
GTGGACACCAACCCGCTGTTAGGTGCCGGCAAATTCGCAACCGACCCGGCAGTGACGTTG
GCGCACGAATTGATTCATGCGGGTCACCGCTTATACGGTATCGCGATCAATCCGAATCGC
GTCTTTAAAGTCAATACCAACGCGTACTACGAAATGAGCGGCTTAGAGGTTAGCTTTGAA
GAATTACGCACCTTCGGTGGCCACGACGCCAAGTTCATCGACAGCCTGCAGGAAAATGAG
TTCCGCTTGTACTATTACAATAAATTCAAGGACATCGCGAGCACCTTAAATAAAGCAAAG
AGCATTGTGGGCACCACCGCAAGCTTGCAGTACATGAAGAACGTATATTAAGGAAAAATAT
TTGTTGTCGGAGGATACCAGCGGGAAATTCAGCGTCGATAAGCTGAAATTCGACAAATTG
TATAAAATGCTGACCGAGATTTACACCGAGGATAACTTCGTCAAGTTTTTTAAGGTGTTA
AATCGTAAGACCTATTTAAACTTTGATAAAGCGGTGTTTAAAATTAATATCGTGCCGAAG
GTGAATTACACCATCTACGATGGTTTCAATTTACGCAACACGAACTCGGCGGCGAATTTT
AATGGCCAAAACACCGAATTAACAACATGAACTTTACGAAGTTAAAGAATTTCACGGGC
TTATTCGAATTCTACAAGTTATTATGCGTGCGCGGCATCATTACCAGCAAGGCAGGTGCG
GGCAAGTCCTTGGTTCCGCGTGGCAGCGCCGGCGCCGGCGCGCTCAATGATCTGTGTATT
AAAGTCAATAACTGGGACCTGTTCTTCAGCCCGAGCGAGGATAACTTTACCAACGACTTA
AACAAAGGCGAGGAGATCACGAGCGATACGAACATCGAGGCGGCGGAGGAAATATTAGC
CTGGACCTCATTCAGCAGTACTATCTGACGTTCAATTTTGACAATGAGCCGGAGAACATC
AGCATTGAAAATCTCAGCAGCGACATCATCGGTCAGTTGGAACTGATGCCGAACATTGAA
CGCTTTCCGAACGGCAAAAAATATGAACTGGACAAGTATACCATGTTCCATTACTTACGC
GCACAGGAATTTGAGCACGGCAAGAGCCGCATTGCGCTGACCAATAGCGTTAACGAGGCC
TTGTTAAATCCGAGCCGTGTCTACACGTTCTTCAGCAGCGATTATGTCAAAAAGTGAAC
AAGGCGACCGAAGCCGCGATGTTTTTGGGCTGGGTCGAGCAATTGGTTTACGATTTTACC
GACGAAACCAGCGAGGTGAGCACGACCGACAAAATTGCAGATATCACCATCATCATTCCG
TACATCGGTCCGGCGCTCAATATCGGCAATATGTTATACAAGGACGACTTTGTGGGCGCG TABLE 1-continued Sequences

```
CTGATCTTTAGCGGCGCGGTTATCTTATTAGAATTCATCCCGGAGATCGCAATCCCGGTC
TTGGGCACCTTTGCGTTGGTGAGCTATATCGCGAATAAAGTGCTCACGGTCCAAACCATC
GATAACGCGCTCAGCAAGCGTAATGAGAAATGGGACGAGGTTTATAAGTATATCGTGACC
AACTGGTTAGCAAAAGTCAATACGCAGATCGATCTCATCCGCAAAAAAATGAAAGAAGCC
TTGGAAAATCAAGCGGAGGCAACCAAAGCCATCATTAATTACCAGTATAACCAATATACC
GAAGAAGAAAAAAACAATATCAACTTCAATATCGATGATTTGAGCAGCAAACTGAACGAG
AGCATTAACAAAGCGATGATTAACATCAACAAGTTCTTGAATCAATGCAGCGTGAGCTAT
CTCATGAACAGCATGATCCCGTATGGCGTCAAACGCTTGGAAGATTTTGACGCCAGCCTG
AAAGATGCGCTCCTCAAGTATATTTATGACAACCGCGGCACCCTCATTGGCCAGGTGGAC
CGCTTGAAGGATAAAGTGAACAATACGCTCAGCACGGATATCCCGTTCCAGCTGAGCAAG
TACGTCGACAACCAGCGCTTACTGAGCACCTTTACCGAGTATATCAAGAACATCATTAAT
ACCAGCATCCTCAACTTGCGCTATGAGAGCAATCACCTGATCGACCTCAGCCGCTACGCC
AGCAAGATCAACATCGGCAGCAAGGTCAATTTCGACCCGATCGATAAGAATCAGATCCAA
TTGTTTAACCTGGAAAGCAGCAAGATCGAGGTTATCTTGAAGAACGCGATTGTGTACAAC
AGCATGTACGAGAACTTTAGCACGAGCTTCTGGATTCGTATCCGCAAGTATTTCAATAGC
ATTAGCCTGAATAACGAATATACCATTATCAACTGCATGGAAAATAATAGCGGCTGGAAG
GTGAGCTTAAATTACGGCGAGATCATTTGGACCTTACAGGATACCCAAGAAATCAAACAG
CGCGTCGTCTTTAAGTATAGCCAGATGATCAACATCAGCGATTACATCAACCGCTGGATC
TTCGTGACCATCACCAATAATCGCTTGAATAATAGCAAGATTTACATCAATGGTCGCTTG
ATTGATCAAAAACCGATCAGCAATCTCGGTAATATCCATGCCAGCAATAACATCATGTTT
AAGTTAGACGGTTGCCGCGATACCCACCGCTATATCTGGATCAAGTATTTTAACTTATTT
GATAAGGAACTCAACGAAAAGGAAATTAAAGACTTATATGACAATCAGAGCAATAGCGGC
ATCCTGAAGGATTTCTGGGGCGACTACCTGCAGTACGATAAGCCGTACTATATGTTGAAC
TTGTATGACCCGAACAAATATGTCGATGTGAACAATGTGGGTATTCGTGGCTATATGTAC
TTAAAGGGCCCGCGTGGTAGCGTGATGACCACGAATATTTACTTAAACAGCAGCTTATAC
CGCGGCACGAAGTTTATTATCAAGAAGTATGCCAGCGGCAACAAGGACAATATCGTCCGC
AACAACGACCGTGTGTATATTAACGTGGTGGTGAAGAATAAAGAGTACCGCTTGGCCACG
AATGCGAGCCAGGCGGGCGTGGAAAAAATCTTGAGCGCGTTGGAGATCCCGGACGTCGGC
AACCTCAGCCAGGTTGTGGTGATGAAGTCTAAAAACGACCAGGGCATCACGAACAAGTGC
AAAATGAATTTGCAAGATAACAACGGCAACGACATCGGCTTTATTGGTTTTCACCAGTTC
AATAACATCGCCAAACTCGTGGCCAGCAATTGGTATAACCGCCAAATTGAACGCAGCAGC
CGCACGCTCGGCTGTAGCTGGGAGTTCATCCCGGTGGACGATGGCTGGGGCGAGCGCCCG
CTCGGAGATCTGGTGCCACGCGGTTCCGCGAATTCGAGCTCCGTCGACAAGCTTTGGAGC
CACCCGCAGTTCGAAAAATAA
SEQ ID NO 12: VPASA100

VPASAVPASAVPASAVPASAVPASAVPASAVPASAVPASAVPASAVPASAVPASAVPASAVP
ASAVPASAVPASAVPASAVPASAVPASAVPASAVPASA

SEQ ID NO 13: VAPSA100
VAPSAVAPSAVAPSAVAPSAVAPSAVAPSAVAPSAVAPSAVAPSAVAPSAVAPSAVAPSAVA
PSAVAPSAVAPSAVAPSAVAPSAVAPSAVAPSAVAPSA

SEQ ID NO 14: VPASA100-rBoNT/A (amino acid sequence)
MGSSHHHHHHGSLVPRSVPASAVPASAVPASAVPASAVPASAVPASAVPASAVPASAVPASA
VPASAVPASAVPASAVPASAVPASAVPASAVPASAVPASAVPASAVPASAVPASAPFVNKQF
NYKDPVNGVDIAYIKIPNAGQMQPVKAFKIHNKIWVIPERDTFTNPEEGDLNPPPEAKQVPV
SYYDSTYLSTDNEKDNYLKGVTKLFERIYSTDLGRMLLTSIVRGIPFWGGSTIDTELKVIDT
NCINVIQPDGSYRSEELNLVIIGPSADIIQFECKSFGHEVLNLTRNGYGSTQYIRFSPDFTF
GFEESLEVDTNPLLGAGKFATDPAVTLAHELIHAGHRLYGIAINPNRVFKVNTNAYYEMSGL
EVSFEELRTFGGHDAKFIDSLQENEFRLYYYNKFKDIASTLNKAKSIVGTTASLQYMKNVFK
EKYLLSEDTSGKFSVDKLKFDKLYKMLTEIYTEDNFVKFFKVLNRKTYLNFDKAVFKINIVP
KVNYTIYDGFNLRNTNLAANFNGQNTEINNMNFTKLKNFTGLFEFYKLLCVRGIITSKAGAG
KSLVPRGSAGAGALNDLCIKVNNWDLFFSPSEDNFTNDLNKGEEITSDIN'EAAEENISLDL
IQQYYLTFNFDNEPENISIENLSSDIIGQLELMPNIERFPNGKKYELDKYTMFHYLRAQEFE
HGKSRIALTNSVNEALLNPSRVYTFFSSDYVKKVNKATEAAMFLGWVEQLVYDFTDETSEVS
TTDKIADITIIIPYIGPALNIGNMLYKDDFVGALIFSGAVILLEFIPEIAIPVLGTFALVSY
IANKVLTVQTIDNALSKRNEKWDEVYKYIVINWLAKVNTQIDLIRKKMKEALENQAEATKAI
INYQYNQYTEEEKNNINFNIDDLSSKLNESINKAMININKFLNQCSVSYLMNSMIPYGVKRL
EDFDASLKDALLKYIYDNRGTLIGQVDRLKDKVNNTLSTDIPFQLSKYVDNQRLLSTFTEYI
KNIINTSILNLRYESNHLIDLSRYASKINIGSKVNFDPIDKNQIQLFNLESSKIEVILKNAI
VYNSMYENFSTSFWIRIPKYFNSISLNNEYTIINCMENNSGWKVSLNYGEIIWTLQDTQEIK
QRVVFKYSQMINISDYINRWIFVTITNNRLNNSKIYINGRLIDQKPISNLGNIHASNNIMPK
LDGCRDTHRYIWIKYFNLFDKELNEKEIKDLYDNQSNSGILKDFWGDYLQYDKPYYMLNYD
PNKYVDVNNVGIRGYMYLKGPRGSVMTTNIYLNSSLYRGTKFIIKKYASGNKDNIVRNNDRV
YINVVVKNKEYRLATNASQAGVEKILSALEIPDVGNLSQVVVMKSKNDQGITNKCKMNLQDN
NGNDIGFIGFHQFNNIAKLVASNWYNRQIERSSRTLGCSWEFIPVDDGWGERPLGDLVPRGS
ANSSSVDKLWSHPQFEK SEQ ID NO 15: VAPSA100-rBoNT/A (amino acid sequence)
MGSSHHHHHHGSLVPRSVAPSAVAPSAVAPSAVAPSAVAPSAVAPSAVAPSAVAPSAVAPSA
VAPSAVAPSAVAPSAVAPSAVAPSAVAPSAVAPSAVAPSAVAPSAVAPSAVAPSAPFVNKQF
NYKDPVNGVDIAYIKIPNAGQMQPVKAFKIHNKIWVIPERDTFTNPEEGDLNPPPEAKQVPV
SYYDSTYLSTDNEKDNYLKGVTKLFERIYSTDLGRMLLTSIVRGIPFWGGSTIDTELKVIDT
NCINVIQPDGSYRSEELNLVIIGPSADIIQFECKSFGHEVLNLTRNGYGSTQYIRFSPDFTF
GFEESLEVDTNPLLGAGKFATDPAVTLAHELIHAGHRLYGIAINPNRVFKVNTNAYYEMSGL
EVSFEELRTFGGHDAKFIDSLQENEFRLYYYNKFKDIASTLNKAKSIVGTTASLQYMKNVFK
EKYLLSEDTSGKFSVDKLKFDKLYKMLTEIYTEDNFVKFFKVLNRKTYLNFDKAVFKINIVP
```

TABLE 1-continued

Sequences

KVNYTIYDGFNLRNTNLAANFNGQNTEINNMNFTKLKNFTGLFEFYKLLCVRGIITSKAGAG
KSLVPRGSAGAGALNDLCIKVNNWDLFFSPSEDNFTNDLNKGEEITSDIN'EAAEENISLDL
IQQYYLTFNFDNEPENISIENLSSDIIGQLELMPNIERFPNGKKYELDKYTMFHYLRAQEFE
HGKSRIALTNSVNEALLNPSRVYTFFSSDYVKKVNKATEAAMFLGWVEQLVYDFTDETSEVS
TTDKIADITIIIPYIGPALNIGNMLYKDDFVGALIFSGAVILLEFIPEIAIPVLGTFALVSY
IANKVLTVQTIDNALSKRNEKWDEVYKYIVINWLAKVNTQIDLIRKKMKEALENQAEATKAI
INYQYNQYTEEEKNNINFNIDDLSSKLNESINKAMININKFLNQCSVSYLMNSMIPYGVKRL
EDFDASLKDALLKYIYDNRGTLIGQVDRLKDKVNNTLSTDIPFQLSKYVDNQRLLSTFTEYI
KNIINTSILNLRYESNHLIDLSRYASKINIGSKVNFDPIDKNQIQLFNLESSKIEVILKNAI
VYNSMYENFSTSFWIRIPKYFNSISLNNEYTIINCMENNSGWKVSLNYGEIIWTLQDTQEIK
QRVVFKYSQMINISDYINRWIFVTITNNRLNNSKIYINGRLIDQKPISNLGNIHASNNIMFK
LDGCRDTHRYIWIKYFNLFDKELNEKEIKDLYDNQSNSGILKDFWGDYLQYDKPYYMLNLYD
PNKYVDVNNVGIRGYMYLKGPRGSVMTTNIYLNSSLYRGTKFIIKKYASGNKDNIVRNNDRV
YINVVVKNKEYRLATNASQAGVEKILSALEIPDVGNLSQVVVMKSKNDQGITNKCKMNLQDN
NGNDIGFIGFHQFNNIAKLVASNWYNRQIERSSRTLGCSWEFIPVDDGWGERPLGDLVPRGS
ANSSSVDKLWSHPQFEK

The invention claimed is:

1. A recombinant clostridial neurotoxin comprising a protein segment consisting of at least 50 amino acid residues, wherein said protein segment consists of the amino acid sequence $(Xaa)_x-[(P,A,S)_y-(Xaa)-]_z(P,A,S)_y-(Xaa)_x$, wherein Xaa is an amino acid residue independently selected from any naturally occurring amino acid residue, provided that at least one Xaa in $[(P,A,S)_y-(Xaa)-]_z$ is different from an alanine, serine or proline residue; (P,A,S) represents an amino acid residue independently selected from an alanine (A), a serine (S) and a proline (P) residue; x is a number independently selected from 0 and 1; y is a number independently selected from 3 and 4; and z is 9 or more.

2. The recombinant clostridial neurotoxin of claim 1, wherein said protein segment comprises an amino acid sequence consisting of between 50 and 3000 amino acid residues.

3. The recombinant clostridial neurotoxin of claim 1, wherein the proline residues comprised in said protein segment constitute more than 4% and less than 40% of the amino acids of said protein segment.

4. The recombinant clostridial neurotoxin of claim 1, wherein said protein segment comprises at least one amino acid sequence selected from the group consisting of: $(VPASA)_{20}$ (SEQ ID NO: 12) and $(VAPSA)_{20}$ (SEQ ID NO: 13); or circular permuted versions or (a) multimer(s) of these sequences as a whole or parts of these sequences.

5. The recombinant clostridial neurotoxin of claim 1, wherein said protein segment is inserted at (i) the N-terminus of the light chain of said recombinant clostridial neurotoxin; (ii) the C-terminus of the light chain of said recombinant clostridial neurotoxin; (iii) the N-terminus of the heavy chain of said recombinant clostridial neurotoxin; or (iv) the C-terminus of the heavy chain of said recombinant clostridial neurotoxin.

6. The recombinant clostridial neurotoxin of claim 1, wherein the sequence of said clostridial neurotoxin is selected from the sequence of (i) a *Clostridium botulinum* neurotoxin serotype A, B, C, D, E, F, and G, (ii) a functional variant of a *Clostridium botulinum* neurotoxin of (i), or (iii) a chimeric *Clostridium botulinum* neurotoxin, wherein the clostridial neurotoxin light chain and heavy chain are from different clostridial neurotoxin serotypes.

7. The recombinant clostridial neurotoxin of claim 1, wherein said recombinant clostridial neurotoxin shows increased duration of effect relative to an identical clostridial neurotoxin without said protein segment.

8. The recombinant clostridial neurotoxin of claim 1, wherein the recombinant clostridial neurotoxin causes longer lasting denervation relative to an identical clostridial neurotoxin without said protein segment.

9. A pharmaceutical composition comprising the recombinant clostridial neurotoxin of claim 1.

10. A method for cosmetic treatment comprising administering a recombinant clostridial neurotoxin of claim 1 to a patient in need thereof.

11. A method for the generation of a recombinant clostridial neurotoxin, said method comprising obtaining a recombinant nucleic acid sequence encoding a recombinant single-chain precursor clostridial neurotoxin by the insertion of a nucleic acid sequence encoding the protein segment according to claim 1 into a nucleic acid sequence encoding a parental clostridial neurotoxin.

12. A recombinant single-chain clostridial neurotoxin precursor for a disulfide-linked di-chain clostridial neurotoxin, comprising a functionally active clostridial neurotoxin light chain, a functionally active neurotoxin heavy chain, a loop region linking the C-terminus of the light chain with the N-terminus of the heavy chain, and protein segment as defined in claim 1.

13. A nucleic acid sequence encoding the recombinant single-chain clostridial neurotoxin of claim 12.

14. A method for obtaining the nucleic acid sequence of claim 13, comprising inserting a nucleic acid sequence encoding said protein segment into a nucleic acid sequence encoding a parental clostridial neurotoxin.

15. A vector comprising the nucleic acid sequence of claim 13, or the nucleic acid sequence obtainable by a method comprising inserting a nucleic acid sequence encoding said protein segment into a nucleic acid sequence encoding a parental clostridial neurotoxin.

16. A recombinant host cell comprising the nucleic acid sequence of claim 13, the nucleic acid sequence obtainable by the method comprising inserting a nucleic acid sequence encoding said protein segment into a nucleic acid sequence encoding a parental clostridial neurotoxin, or a vector comprising said sequence.

17. A method for producing the recombinant single-chain precursor clostridial neurotoxin of claim 12, comprising expressing a nucleic acid sequence encoding the recombinant single-chain clostridial neurotoxin.

18. The recombinant clostridial neurotoxin of claim 1, wherein Xaa is valine and wherein z is a number between 9 and 750.

19. The recombinant clostridial neurotoxin of claim 1, wherein said protein segment comprises an amino acid sequence consisting of between 90 and 220 amino acid residues.

20. The recombinant clostridial neurotoxin of claim 1, wherein said protein segment comprises (VPASA)$_{20}$ (SEQ ID NO: 12).

21. The recombinant clostridial neurotoxin of claim 1, wherein said protein segment is inserted at the N-terminus of the light chain of said recombinant clostridial neurotoxin.

22. The recombinant clostridial neurotoxin of claim 1, wherein the sequence of said clostridial neurotoxin is the sequence of *Clostridium botulinum* neurotoxin serotype A.

23. The recombinant clostridial neurotoxin of claim 1, wherein said recombinant clostridial neurotoxin has a light chain and a heavy chain comprised in the amino acid sequence of SEQ ID NO: 14 or SEQ ID NO: 15.

24. The method according to claim 11, wherein said method further comprises heterologously expressing said recombinant nucleic acid sequence in a host cell.

25. The method according to claim 24, wherein said host cell is a bacterial host cell.

26. The method according to claim 25, wherein said bacterial host cell is *Escherichia coli*.

27. The recombinant single-chain clostridial neurotoxin precursor for a disulfide-linked di-chain clostridial neurotoxin of claim 12, wherein the sequence of said clostridial neurotoxin is selected from the sequence of (i) a *Clostridium botulinum* neurotoxin serotype A, B, C, D, E, F, and G, (ii) a functional variant of a *Clostridium botulinum* neurotoxin of (i), or (iii) a chimeric *Clostridium botulinum* neurotoxin, wherein the clostridial neurotoxin light chain and heavy chain are from different clostridial neurotoxin serotypes.

* * * * *